United States Patent [19]

Scott et al.

[11] Patent Number: 5,025,222

[45] Date of Patent: Jun. 18, 1991

[54] SYSTEM AND METHOD FOR MONITORING SUBSTANCES AND REACTIONS

[75] Inventors: Bentley N. Scott, Richardson; Samuel R. Shortes, Lewisville, both of Tex.

[73] Assignee: Phase Dynamics, Inc., Richardson, Tex.

[21] Appl. No.: 442,980

[22] Filed: Nov. 27, 1989

Related U.S. Application Data

[63] Continuation-in-part of Ser. No. 376,782, Jul. 7, 1989, Pat. No. 4,996,490, which is a continuation-in-part of Ser. No. 932,068, Nov. 18, 1986, Pat. No. 4,862,060.

[51] Int. Cl.⁵ ......................................... G01R 27/26
[52] U.S. Cl. .............................. 324/639; 73/61.1 R; 324/641; 324/633
[58] Field of Search ............... 324/633, 639, 640, 641, 324/674, 675; 73/61 R, 61.1 R

[56] References Cited

U.S. PATENT DOCUMENTS

| | | | |
|---|---|---|---|
| 2,755,436 | 7/1956 | Heinz | 324/641 |
| 3,464,005 | 8/1969 | Wood | 324/675 |
| 3,965,416 | 6/1976 | Friedman | 324/682 |
| 4,396,062 | 8/1983 | Iskander | 324/642 |
| 4,499,418 | 2/1985 | Helms et al. | 73/61.1 R |

*Primary Examiner*—Kenneth A. Wieder
*Assistant Examiner*—Maura K. Regan
*Attorney, Agent, or Firm*—Worsham, Forsythe, Sampels & Wooldridge

[57] ABSTRACT

A system and method for monitoring conditions in a fluid medium. A stream of the fluid medium is flowed through a fluid container which is electrically configured as a transmission line segment and which is electrically connected to load to UHF or microwave oscillator. The oscillator is *not* isolated from the load, and is operated free-running, at a starting frequency which is chosen to provide a particularly strong shift in permittivity of the fluid medium, as the chemical reaction progresses. Preferably the frequency and insertion loss of the oscillator are monitored, to gauge the progress of the reaction.

14 Claims, 18 Drawing Sheets

ADDITION REACTION

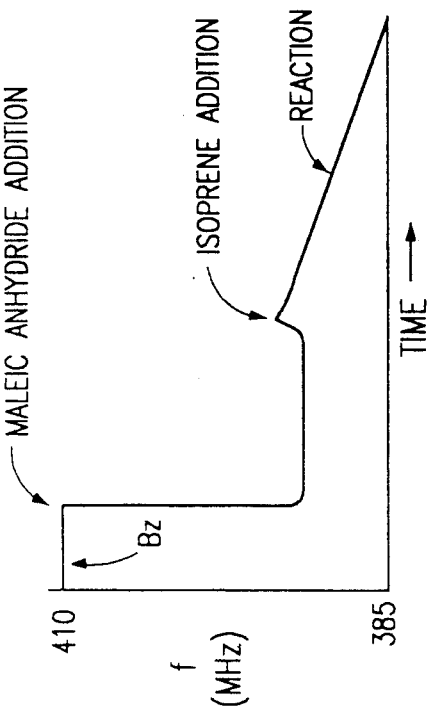
FIG. 12B
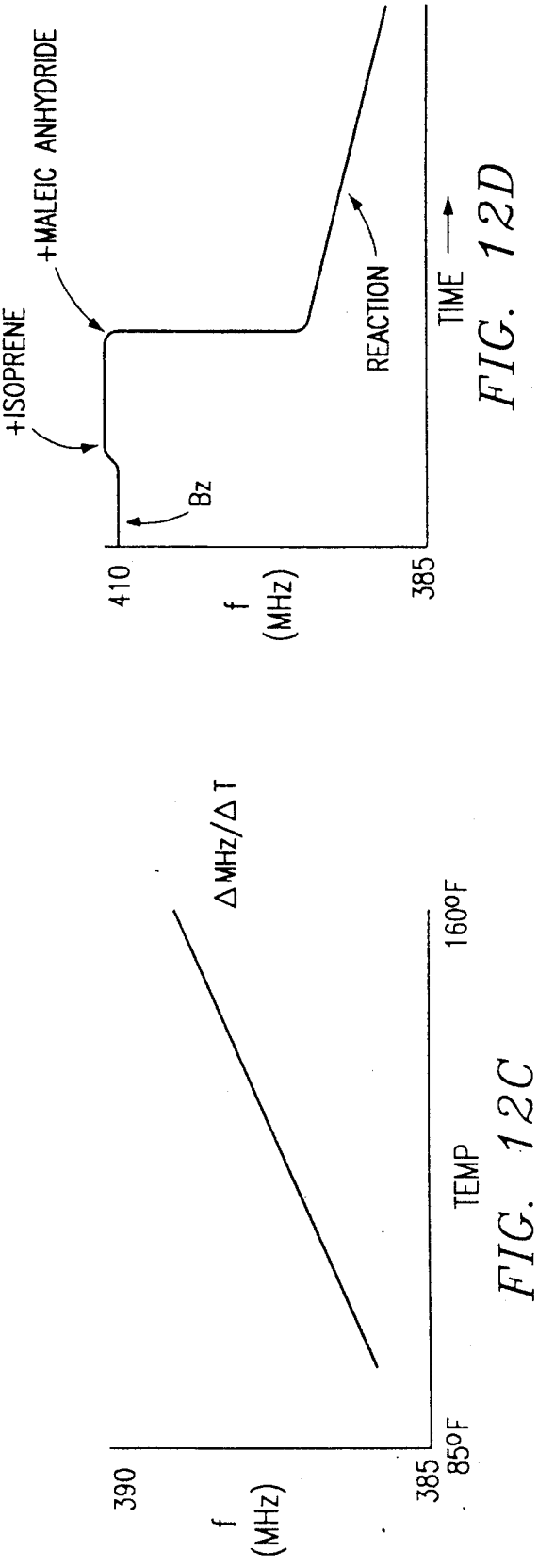
FIG. 12D
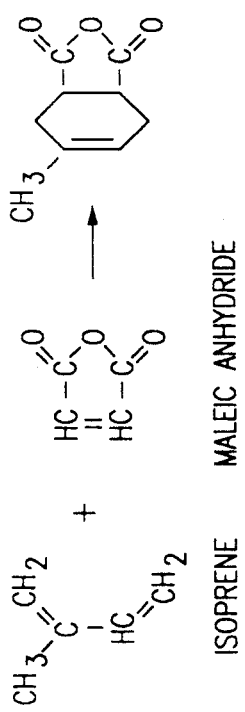
FIG. 12A
FIG. 12C

STYRENE  MALEIC ANHYDRIDE

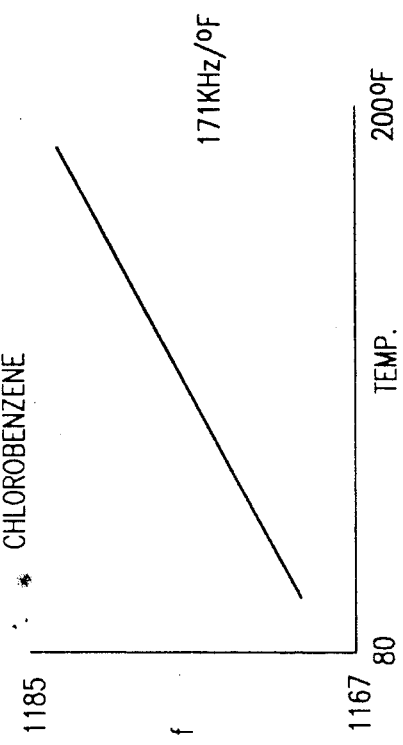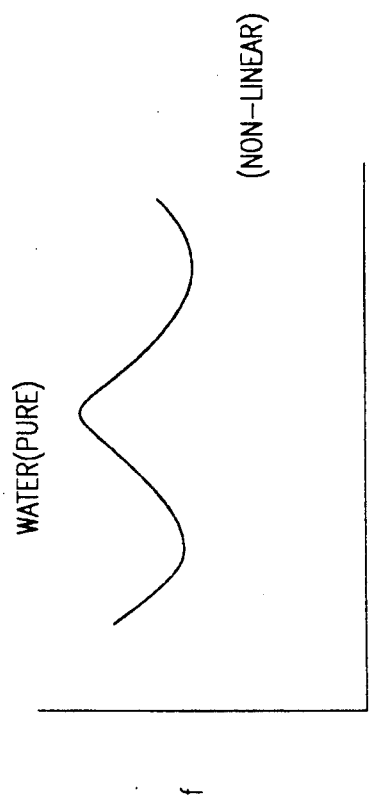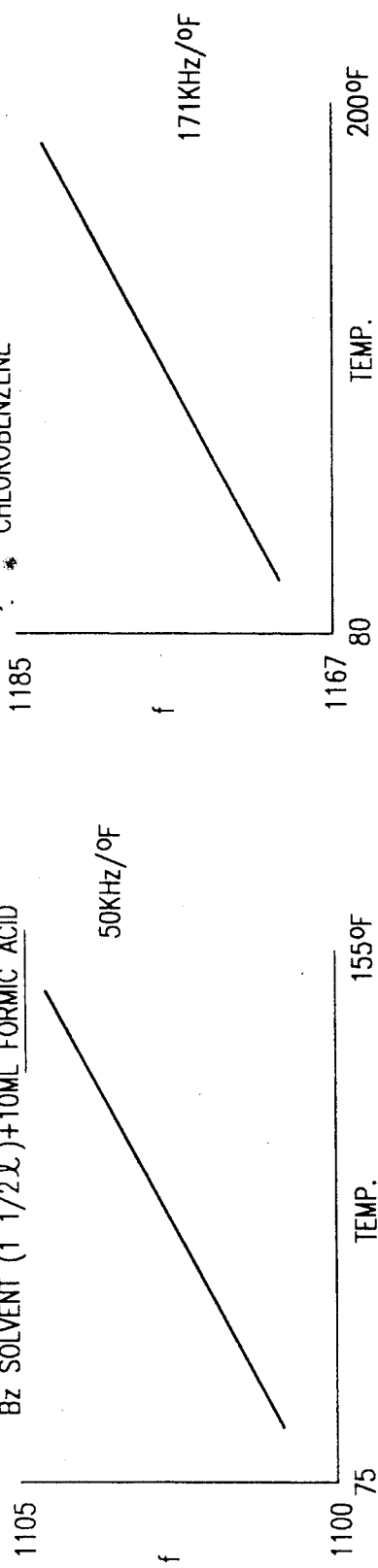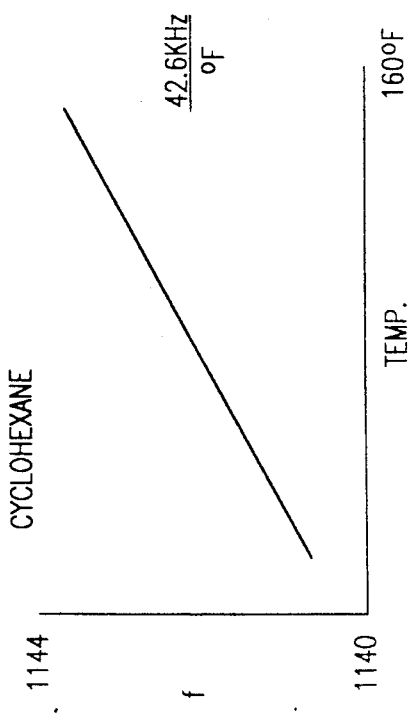
VARIOUS COMPOUNDS vs TEMPERATURE
FIG. 16A
FIG. 16B
FIG. 16C
FIG. 16D

SUBSTITUTION REACTION

SYSTEM AND METHOD FOR MONITORING SUBSTANCES AND REACTIONS

CROSS-REFERENCE TO OTHER APPLICATIONS

The present application is a continuation-in-part of Ser. No. 376,782 filed 7/7/89, now U.S. Pat. No. 4,996,490, which is a continuation-in-part of Ser. No. 932,068, filed 11/18/86, and now issued by U.S. Pat. No. 4,862,060; which are hereby incorporated by reference.

BACKGROUND AND SUMMARY OF THE INVENTION

The present invention relates to systems and methods for monitoring chemical reactions and/or changes in the composition and/or phase of chemical substances or mixtures.

ELECTRICAL METHODS OF CHARACTERIZATION

The grandparent application (Ser. No. 932,068, Filed 11/18/86 and now issued as U.S. Pat. No. 4,862,060) described a novel to measure the water content to crude oil as it comes out of the ground. This system included a short section of piping, mechanically connected so that the fluid stream to be characterized would pass through it, and electrically connected to function as a transmission line (in the electrical sense)[1] in the feedback path of an oscillator. The oscillator was operated as a "free-running" oscillator (for reasons which will be explained below), and this system provided a very sensitive apparatus for monitoring changes (such as changes in the fraction of salt water) in the crude oil coming out of the ground.[2]

[1] A Simple electrical circuit, at low frequencies, can be analyzed as a network of discrete lumped elements, and the propagation delays between elements can be ignored. However, at higher RF or microwave frequencies, this model is inadequate. A different and complementary way to analyze some electrical components or circuits is to model them as a "transmission line," i.e. an extended structure which has a *distributed* resistance and reactance over a finite length. Such structures behave quite differently from discrete lumped networks. An ideal uniform transmission line is completely descried (electrically) by only two parameters: the phase velocity $V_p$ and the characteristic impedance $Z_0$.

[2] An electrical oscillator must include a gain element, and a feedback path which couples the gain element's output back to the gain element's input (at least partly). The oscillator will operate at the frequency (or frequencies) where the total phase shift (through the gain element and the feedback path) is equal to an integral multiple of 360° ($2\pi$ radians).

The system and the methods disclosed in the present application provide a generally applicable method for monitoring the characteristics of a substance which includes a material (or a process flow) of interest, and also is connected electrically as part of the feedback path of an RF oscillator. Changes in the oscillation frequency provided a sensitive indicator of changes in the substance in the container. The container, in the presently preferred embodiment, is shaped as a segment of coaxial line through which fluid materials flow lengthwise, but other shapes can be used instead.

THE "LOAD-PULL" EFFECT

It is well known to electrical engineers generally (and particularly to microwave engineers) that the frequency of an RF oscillator can be "pulled" (i.e. shifted from the frequency of oscillation which would be seen if the oscillator were coupled to an ideal impedance-matched pure resistance), if the oscillator sees an impedance which is different from the ideal matched impedance. Thus, a varying load impedance may cause the oscillator frequency to shift[3].

[3] Any electrical oscillator can be "pulled" to some extent — that is, its frequency can be shifted — by changing the net impedance seen by the oscillator. However, in many systems which use oscillators, pulling of a resonant circuit's frequency is undesirable. An oscillator which is too easily pulled may be overly susceptible to irrelevant external circumstances, such as changes in parasitic capacitance due to human proximity or temperature change. Normal techniques to avoid oscillator pulling include using isolation/buffering circuits between the oscillator and the variable load, and/or using a high-Q tuned circuit to stabilize the oscillator. vary as the characteristics of the material in the electromagnetic propagation structure varies. As this complex impedance changes, the oscillator frequency will vary. Thus, the frequency variation (which can easily be measured) can reflect changes in density (due to bonding changes, addition of additional molecular chains, etc.), ionic content, dielectric constant, or microwave loss characteristics of the medium under study. These changes will "pull" the resonant frequency of the oscillator system. Changes in the medium's magnetic permeability will also tend to cause a frequency change, since the propagation of the RF energy is an electromagnetic process which is coupled to both electric fields and magnetic fields within the transmission line.

[4] An unbuffered oscillator is a oscillator without buffer amplifiers or attenuators. Amplifiers boost the output power and provide isolation from the load impedance changes. Attenuators decrease the amplitude while providing an isolation of two times the attenuation. In the load pulled oscillator configuration the oscillator feedback path that supplies the phase shift needed for oscillation is separated from the load.

[5] A "complex" number is one which can be written as $A+Bi$, where A is the number's "real" part, B is the number's "imaginary" part, and $i^2=-1$. These numbers are added according to the rule $$(A+Bi)+(C+Di)=(A+C)+(B+D)i,$$

and are multiplied according to the rule $$(A+Bi)(C+Di)=(AC-BD)+(AD+BC)i.$$

Complex numbers are used in representing many electrical parameters. For example, impedance can be represented as a complex number whose real part is the resistance, and whose imaginary part is equal to the reactance (inductance or capacitance).

Similarly, permittivity can be represented as a complex number whose imaginary part represents resistive loss, and whose real part represents reactive loading, by the medium, of the propagating electromagnetic wave.

PROPERTIES OF A DIELECTRIC IN A TRANSMISSION LINE

To help explain the use of the load-pull effect in the disclosed innovations, the electromagnetics of a dielectric-loaded transmission line will first be reviewed. If a transmission line is (electrically) loaded with a dielectric material (as, for example, the measurement section of the apparatus of FIG. 1 is loaded by the liquid flowing through the cavity), changes in the composition of the dielectric material may cause electrical changes in the properties of the line. In particular, the impedance of the line, and the phase velocity of wave propagation in the line, may change.

This can be most readily illustrated by first considering propagation of a plane wave in free space. The propagation of a time-harmonic plane were (of frequency f) in a uniform material will satisfy the reduced wave equation $$(\nabla^2+k^2)E=(\nabla^2+k^2)H=0,$$

where

E is the electric field (vector),
H is the magnetic field (vector), and
$\nabla^2$ represents the sum of second partial derivatives along the three spatial axes.

This equation can be solved to define the electric field vector E, at any point r and time t, as $$E(r,t)=E_0\exp[i(k\cdot r-\omega t)],$$

where k is a wave propagation vector which points in the direction of propagation and has a magnitude equal to the wave number k, and $\omega$ = Angular Frequency = $2\pi f$.

In a vacuum, the wave number k has a value "$k_0$" which is $$k_0 = \omega/c$$
$$= \omega(\mu_0\epsilon_0)^{\frac{1}{2}},$$

where $\mu_0$ = Magnetic Permeability of vacuum ($4\pi \times 10^{-7}$ Henrys per meter),
$\epsilon_0$ = Electric Permittivity of vacuum ($1/36\pi) \times 10^{-9}$ Farads per meter), and
c = Speed of light = $(\mu_0\epsilon_0)^{-\frac{1}{2}} = 2.998 \times 10^8$ meters/second.

However, in a dielectric material, the wave number k is not equal to $k_0$; instead $$k = \omega/(c(\mu_r\epsilon_r)^{\frac{1}{2}})$$
$$= \omega(\mu_0\mu_r\epsilon_0\epsilon_r)^{\frac{1}{2}},$$

where $\mu_r$ = *Relative* Permeability of the material (normalized to the permeability $\mu_0$ of a vacuum), and
$\epsilon_r$ = *Relative* Permittivity of the material (normalized to the permittivity $\epsilon_0$ of a vacuum).

Thus, if the relative permeability $\mu_r$ and/or the relative permittivity $\epsilon_r$ vary, the wave number k and the wave propagation vector k will also vary, and this variation will typically affect the load pulled oscillator frequency.[6]

[6] The full analysis of the wave propagation in a cavity or at a boundary is much more complex, but in any case wave propagation will depend on the wave number, and the foregoing equations show how the wave number k can vary as the medium changes. See generally, e.g., R. Elliott, *Electromagnetics* (1966); J. Jackson, *Classical Electrodynamics* (2d ed. 1975); G. Tyras, *Radiation and Propagation of Electromagnetic Waves* (1969); R. Mittra & S. Lee, *Analytical Techniqes in the Theory of Guided Waves* (1971); L. Lewin, *Theory of Waveguides* (1975); all of the which are hereby incorporated by reference.

FREQUENCY HOPPING IN A LOAD-PULLED OSCILLATOR

In a typical free-running oscillator, the oscillator frequency is defined by a resonant feedback circuit (the "tank" circuit), and can also be pulled slightly by a reactive load,[7] as noted above. Thus, such an oscillator can be broadly tuned by including a varactor in the tank circuit.[8]

[7] The degree by which the reactive load can change the oscillator's frequency will depend on the coupling coefficient between the load and the tank circuit. Thus, an increased coupling coefficient means that the oscillator frequency will be more sensitive to changes in the load element. However, the coupling coefficient should not be increased to the point where spectral breakup (multiple frequency operation) occurs, since this would render the desired measurement of the oscillator signal impossible.

[8] This is one type of voltage-controlled oscillator (VCO), is preferably a shorted transmission line segment) will change. This phase difference will be equal to an extract multiple of 180° at any frequency where the electrical length of the transmission line segment is an exact multiple of $\lambda/4$.

As the oscillator frequency passes through such a frequency (i.e. one where the transmission line segment's electrical length is equal to a multiple of $\lambda/4$), the load's net impedance will change from inductive to capacitive (or vice versa). As this occurs, the frequency of the oscillator may change abruptly rather than smoothly.[9] This jump in frequency will be referred to as a frequency "hop".[10]

[9] This change in frequency, as the load goes from capacitive ($-180°$) to inductive ($+180°$) or vice versa, is instantaneous *if* the equivalent parallel resistive part is large (e.g. greater than approximately 500 ohms in a 50 ohm system).

[10] The amount by which the frequency shifts during the "hop" will depend on the Q of the load element (as seen by the oscillator circuit), and on the coupling coefficient between the load element and the tank circuit.

For a transmission line of length 1 which contains a dielectric material of relative dielectric constant $\epsilon_r$, the frequency at which one full wavelength ($1\lambda$) exists in the transmission line is equal to c (the speed of light in vacuum, which is $2.995 \times 10^8$ meters/second) divided by the length of the line in meters and by the square root of the relative dielectric constant of the material.

$$\text{Frequency}_{1\lambda} = c/(l\epsilon_4^{\frac{1}{2}}).$$

For example, for a one-foot-long line filled with a material having $\epsilon_r = 1$, $l = 12$ inches ($=0.3048$ meters), and $$\text{Frequency}_{1\lambda} = (2.995 \times 10^8)/(0.3048 \times 1.0) \approx 980 \text{ MHz}.$$

However, since one wavelength actually contains two excursions from inductive to capacitive reactive impedances, only one-half wavelength is required to see one frequency hop of the load pulled oscillator. If the transmission line is terminated into a short or an open, the resulting effective length is increased to twice the actual length, since a standing wave is generated (due to the energy incident at the short or open being reflected back to the input of the transmission line). In essence, the energy travels down the line, gets reflected, and travels back to the input. With this taken into account, the first frequency with a wavelength long enough to cause a frequency "hop" of the oscillator is one fourth the length calculated above, or 245 MHz.

Multiples of this first quarter-wavelength frequency will also cause the impedance seen at the input to the transmitted line to go from inductive to capacitive reactance. The longer the transmission line, the greater the number of phase transitions that will occur. Longer line length also multiples the phase changes that are brought about by a change in the dielectric constant. For every one-quarter wavelength change in the effective (electrical) length of the line, the complex impedance seen at the oscillator changes by 180°.

For example, suppose that a given oscillator, coupled into a low loss load with an electrical length of one-quarter wavelength ($\lambda/4$), provides 50 MHz of load pulling frequency change (total excursion through all phases). If the monitored material changes enough to produce a change of only one degree of phase in the electrical length of the load, the oscillator frequency will change by 138.9 kHz. The represents an absolute resolution of $7.2 \times 10^{-6}$ degrees of phase change for each Hertz of sensitivity.[11] For every additional quarter wavelength of line length, this sensitivity to phase is multiplied by 1.5. This is due to the change in phase being an additive function of every additional quarter wave in the measurement section.

[11] Even if the resolution of frequency measurement is only $\pm 100$ Hz, this would still give an accuracy of better than one-thousandth of one degree. This is vastly better resolution than is possible with vector impedance systems (such as an HP 8510 Network Analyzer).

FIG. 7 shows a typical tuning frequency versus voltage plot for a VCO loaded into a shorted transmission line. The height of the "hop" can be measured by holding the VCO tuning voltage constant, while a transmission line terminated into a short is varied in length[12] to cause a full rotation of the impedance vector seen at the VCO's input port. The resulting data of frequency versus length of the transmission line will show a jump in frequency (a delta frequency from the bottom of the "hop" to the top of the "hop") which coincides with the delta frequency of the "hop" seen when the VCO was swept using the tuning voltage.

[12]Such variable transmission lines are commonly used in the microwave industry, and are referred to as "line stretchers."

Thus, if the VCO is swept across a frequency band and the number of frequency "hops" was counted, the number of "hops" reveals the number of wavelengths in the transmission line.—

[13]More precisely, it will be found that the wavelengths at which hops are observed are separated from each other by one-quarter of the effective (electrical) length of the measurement section.

This provides a means for determination of the range of dielectric constant change in a medium even when it rotates the phase vector multiple times (and therefore, the oscillator frequency returns to the same value multiple times). If the dielectric constant of the material in the transmission line is increased, then the above equations show that the frequency of the first full wavelength is decreased by the square root of the dielectric constant. Additionally, this means that the number of wavelengths at a fixed frequency increases with increasing dielectric constant. These facts simply that the VCO tuning curve will see more "hops" as the dielectric constant is increased due to the increasing fraction or whole wavelengths encountered.

Ideally, the oscillator will not cease oscillations (or break into multiple frequency oscillation or spectral breakup) into any load regardless of the load characteristics. However, this is not a strictly necessary conditions for use of the disclosed method and system innovations.[14]

[14]The second harmonic of the oscillator frequency is typically enhanced (becoming greater in amplitude than the fundamental frequency) just before the shift from inductive to capacitive impedance (or vice versa), due to the extreme non-linearities at this point. This does not hinder the use of load pulling as a measurement technique, since the measurement is typically made outside of this region of the impedance shift from inductive to capacitive. Alternatively, the second harmonic may be filtered out of the measurement.

MEASUREMENT OF SUBSTANCES WITH A HIGH MICROWAVE LOSS FACTOR

A measure of the dielectric loss of a materials is typically given as the dielectric loss tangent (a unitless number) which is defined as the tangent of the imaginary part divided by the real part of the complex dielectric constant. Low loss materials are typically below a loss tangent equal to or less than 0.01. When the disclosed systems are used to measure materials with a high loss factor, the material's absorption begins to dominate the load versus frequency effects, but a measurement capability still exists due to the sensitivity of the load pulling method.

However, a potential problem with highly conductive materials in an apparatus like that of FIG. 1 is that the observed loss of the system may decrease for more lossy materials, since the reflection at the interface between the material under study and the microwave transition section will increase. A solution to this problem is outlined in parent application Ser. No. 376,782 filed 7/7/89. As taught therein, a very good dielectric material is added as a sheath around the coaxial center conductor. This material prevents the electric field from going to zero immediately near the center conductor of the transmission line (which could otherwise occur, due to the highly conductive medium under study shorting out the electric field to the outer conductor wall). With the dielectric material as a sheath, propagation along the center rod can occur with slight loss and a small penetration of the good conductor material of the center rod. On the outer portion of the dielectric interface, the medium under study becomes the virtual outer wall of the coaxial conductor with a skin depth of propagation which encompasses the entire medium under study and terminates on the actual outer metal wall of the coaxial line. The resultant changes in the complex dielectric constant are still reflected in a change in the complex load impedance seen at the load pull oscillator and a measurement is still viable.

ADDITIONAL INFORMATION FROM LOAD PULL MEASUREMENT

The disclosed innovative system and method also permits other information to be derived, regarding the substance being monitored.

DIFFERENCE IN OPERATION FREQUENCY

Additional information can be obtained by retuning the VCO, so that the frequency is forced to change, and making another measurement at a much higher frequency. Since materials change properties versus frequency, the amount of frequency change due to load pulling will vary versus the frequency of operation.

A VCO will typically be designed to cover approximately one octave above its turn on frequency. If a VCO would not give enough frequency change to see the desired range of varying parameters versus operating frequency, an additional unbuffered oscillator, which runs at any frequency required to obtain appropriate data, may be switched into the coaxial line.

When two widely spaced frequencies are measured for a medium under study with a load pulled oscillator, the difference (delta) frequency between these two measurements will be unique for a given medium. This phenomena will aid in distinguishing constituents and the progress of mixing or reaction.

MONITORING OF INSERTION LOSS

If the incident power and the reflected power is measured in a system where the final load is a short, the difference in powers is the insertion loss of the medium multiplied by a factor of two (since this power difference is caused by two transits through due to the path down to the short and return is a path length twice through the medium of interest). The insertion loss measurement will aid in determination of the charging conductivity of the medium or its change in absorption of the RF energy. This information can be related to the mixing or reaction products to further distinguish unique situations where the frequency change of the load pulled oscillator is not enough information or resolution by itself.

EFFECT OF COMPLEX PERMEABILITY

The magnetic permeability $\mu_r$ can also be dynamically measured by the disclosed techniques. Since the velocity varies with $(\mu_r \epsilon_r)^{-\frac{1}{2}}$, changes in $\mu_r$ will change the phase shift through a given physical length of line, and thus change the frequency of the oscillator.

A sample-containing waveguide, like that of the principally preferred embodiment, will typically have locations where the electric field is strong but the magnetic field is zero; at such locations only permittivity will affect the oscillator load pull frequency. However, there will also commonly be locations in a waveguide where the magnetic fields are locally strong and electric field is zero: at these locations, only the permeability will affect the propagation characteristics of the transmission line (and therefor contribute to the oscillator frequency).

A system can be built to sample (primarily) one of these parameters. For example, to sample the permeability, the coaxial transmission line will be terminated into a short where the medium of interest is located only in close proximity to the short. A waveguide structure supports very well defined electrical and magnetic field functions, and the sample can be suitably placed in such a structure to measure primarily the permeability.

Typical compounds and substances to do not have varying magnetic permeabilities and therefore, most of the discussion will involve the changing complex permittivity. But, the effects of changing complex permeability will create similar changes in the oscillator load pulling characteristics. If a substance such as barium titanate is studied, the effect of the changing permeability must be considered along with the change in permittivity unless the system is designed specifically to measure only one of these.

THE MEASUREMENT SECTION

The transmission line selected for the majority of the measurements was a coaxial line due to its simple transverse electromagnetic (TEM) mode of propagation. The TEM mode is the simplest mode to set up and to maintain under varying conditions. If other modes were excited by a perturbation, the energy may not be recovered and therefore the information would be lost to the measurement. The coaxial line lends itself to a easily built and modified system which can encompass vast material changes to optimize both the measurement and the environmental conditions that it must work under. The diameter of the rod and the terminations may be easily altered to improve sensitivity by matching of the impedances thereby transferring more of the RF energy into the medium under study.

Addition of a good dielectric as a sheath to the center rod will provide measurements for highly conductive substances under study. The sheath must be thick enough to provide a stable field pattern between the center conductor and the conductive medium under study. The effect of adding this sheath is to in effect make the measurement as a function of the wave propagated as a skin depth in the conductive medium under study which is theoretically equal to or greater than the actual distance between the sheath and the outer coaxial wall.

If the dielectric constant of the material in the transmission line is increased, then the above equations shows that the frequency of the first full wavelength is decreased by the square root of the dielectric constant. This implies that the VCO tuning curve will see more "hops" as the dielectric constant is increased due to the increasing fraction or whole wavelengths encountered.

COUPLING THE ACTIVE DEVICE

An unusual feature of the oscillator configuration used with the present invention is the separation of the load of interest from the resonant circuit proper. The configuration used isolates the two through the active device. It is the non-linear behavior of the transistor that provides the changes in frequency as the load is changed. The loop gain of an oscillator must be unity with an appropriate phase shift to cancel the negative impedance's imaginary part[15] around the resonant loop. The initial gain of the active device must be greater than unity before oscillations can begin in order for the oscillator to be self starting. This extra gain is reduced to unity by the saturation of the active device upon establishment of the oscillations. Saturation of a device normally also changes the phase shift through the device[16]. This requires a change in the operation frequency as the load changes due to the shift in loop gain and phase by the saturated condition change in the active device.

[15] In a simple resistor, an increase in the current passing through the resistor will produce an increase in the voltage across the resistor. By contrast, in microwave gain diodes (or in a transistor with feedback connections) which is operating at less than its saturated current, a small transient increase in the current across the device will produce a *reduction* in the voltage across the device. Thus, since a simple resistor has a positive impedance, such gain devices are referred to as having a negative impedance.

[16] As the gain device approaches saturation, the physics of its operation will gradually change. These changes may cause the phase shift across the gain device to vary significantly. Note that, in the saturation regime, the gain device behaves as a *non-linear* circuit element.

SPECTRAL PURITY OF OSCILLATOR

It has been discovered that, in a system using a free-running oscillator as described above, spectral purity of the oscillator is an important concern. Many microwave oscillators exhibit "spectral breakup," wherein the spectrum of the oscillator's output actually contains multiple frequencies. In most microwave oscillators this is not a problem, since a tuned feedback element will be used to stabilize the gain element, and/or isolation of buffering stages are used to prevent the oscillator's feedback loop from being perturbed by extraneous resonances. However, in the preferred system, since such isolation stages are not used, spectral purity turns out to be quite important. For example, a spurious resonance in the feedback loop (e.g. due to a low-quality RF choke, or due to two impedance mismatches) can permit the oscillator to hop to a frequency which is determined (at least partly) by a harmonic of the spurious resonance, in which case the degree to which the oscillator frequency has been pulled by the changing load will be obscured.

In the presently preferred embodiment, a small series resistor is interposed in the RF output of the oscillator, before the measurement section connection. This resistor adds a small amount of damping, which helps to suppress oscillation at secondary frequencies).

Also, in the presently preferred embodiment, a shunt resistor is attached to the RF output of the oscillator. This resistor also added to stability, by fixing a maximum magnitude for the load impedance seen at the RF output line.[17]

[17] At frequencies where the length of the transmission line segment is a multiple of $\lambda/4$, its impedance can become very large.

PREVIOUS ATTEMPTS AT ELECTRICAL CHARACTERIZATION

Various types of apparatus have been proposed for measuring the concentration of one substances in another, particularly the concentration of a liquid or flowable substance in another liquid or flowable substance. Various devices which utilize the broad concept of determining composition of matter by measuring changes in a microwave signal are disclosed in U.S. Pat. Nos. 3,498,112 to Howard; 3,693,079 to Walker; 4,206,399 to Fitzky et al.; 4,311,957 to Hewitt et al.; 4,361,801 to Meyer et al.; 4,240,028 to Davis Jr.; 4,352,288 to Paap et al.; 4,499,418 to Helms et al.; and 4,367,440 and 4,429,273, both to Mazzagatti; all of which are hereby incorporated by reference.

Although various systems utilizing microwave transmissivity or signal alteration characteristics have been proposed in the prior art, certain considerations in utilizing microwave energy to detect the presence of the concentration of one medium in another have not been met by prior art apparatus. In particular, it is desirable in certain instances to be able to accurately measure, on a continuous basis, the concentration or change in concentration of one fluid in another and particularly where the concentration of one fluid is a very low percentage of the total fluid flow rate or fluid mixture quantity. It is also desirable that the signal change caused by the presence of one substance or medium in another be easily measured and be relatively error free, again, particularly in instances where measurements of low concentrations of one substance such as a fluid another substance such as another fluid are being taken. Moreover, it is important to be able to transmit the microwave signal through a true cross section of the composition being sampled or measured to enhance the accuracy of the measurement.

Typical systems for capacitive based measurement have a capacitive element, used for parameter determination, as part of the resonant feedback loop around an active device. This method works well with very low loss systems, but oscillation ceases with even slightly lossy measurements. As the frequency is increased into the microwave region, it becomes difficult to configure the resonant feedback loop due to the increase in loss versus frequency and the wavelength becoming comparable to the path length. In this case the frequency is changed directly by the resonance change in the feedback loop which includes the element that consists of the sample to be measured. This frequency change is limited to the characteristics and loss of the feedback path and can only be changed over a narrow frequency range with out cessation of oscillations. This limits the measurement technique to small samples of very low loss.

At higher frequencies (above approximately 100 MHz), the capacitive measurement technique fails to work, due to line lengths and stray capacitances. At such frequencies resonant cavity techniques have been employed. (For example, a sample is placed in a resonant cavity to measure the loss and frequency shift with an external microwave frequency source that can be swept across the resonance with and without the sample in the cavity.) This method uses a highly isolated microwave frequency source which is forced by the user (rather than being pulled by the changing resonance) to change its frequency. This technique too meets substantial difficulties. For example, the use of multiple interfaces without a microwave impedance match at each interface causes extraneous reflections, which tend to hide the desired measurement data. This technique too gives errors with very lossy material, but in this case it is due to the very rounded nature of the resonance curve (which is due to the low Q of the loaded cavity). This rounded curve makes it difficult to determine both the center frequency and the 3 dB rolloff frequency closely enough to be accurate in the measurement.

Another technique which is used encompasses the use of a very sharp rise time pulse to obtain time domain data, from which frequency domain values are then derived through transformation techniques.

In U.S. Pat. No. 4,396,062 to Iskander, entitled Apparatus and Method for Time-Domain Tracking of High-speed Chemical Reactions, the technique used is time domain reflectometry (TDR). This contains a feedback system comprising a measurement of the complex permittivity by TDR means which then forces a change in frequency of the source which is heating the formation to optimize this operation. Additionally it covers the measurement of the complex permittivity by TDR methods.

U.S. Pat. No. 3,965,416 to Friedman appears to teach the use of pulse drivers to excite unstable, bi-stable, or relaxation circuits, and thereby propagate a pulsed signal down a transmission line which contains the medium of interest. The pulse delay is indicative of the dielectric constant of the medium. As in all cases, these are either square wave pulses about zero or positive or negative pulses. The circuit is a pulse delay oscillator where the frequency determining element is a shorted transmission line. The frequency generated is promoted and sustained by the return reflection of each pulse. The circuit will not sustain itself into a load that is lossy, since the re-triggering will not occur without a return signal of sufficient magnitude. In addition, the circuit requires a load which is a DC short in order to complete the DC return path that is required for re-triggering the tunnel diodes.

The frequencies of operation of any pulse system can be represented as a Fourier Series with a maximum frequency which is inversely dependent upon the rise time of the pulse. Therefore, the system covered in the Friedman patent is dependent upon the summation of the frequency response across a wide bandwidth. This causes increased distortion of the return pulse and prevents a selective identification of the dielectric constant versus frequency. This also forces a design of the transmission system to meet stringent criteria to prevent additional reflections across a large bandwidth.

The low frequency limit of the TDR technique is determined by the time window which is a function of the length of the transmission line. The upper extreme is determined by the frequency content of the applied pulse. In the case of this pulse relay line oscillator, the upper frequency is determined to a greater extent by the quality of impedance match (the lack of extra reflections) from the circuit through to the substance under study. These extra reflections would more easily upset the re-triggering at higher frequencies.

In one case (FIG. 1 of Friedman) the return reflection initiates a new pulse from the tunnel diode and therefore sets up a frequency (pulse repetition rate) as new pulses continue to be propagated. This is in essence a monostable multivibrator with the return reflection being the trigger. The problem implied, but not completely covered with this approach, is that due to the delay in pulses, the pulse train can overlap and cause multiple triggers to occur. These are caused by the re-reflections of the original parent pulse. An additional problem is with very lossy dielectrics, which will not provide enough feedback signal to initiate the next pulse. If the dielectric medium is of high enough dielectric constant to contain more than one wavelength, or if the dielectric constant of the samples vary greatly, multiple return reflections will alter the behavior of the circuit to render it useless due to the interfering train of return and parent pulses.

FIG. 3 of Friedman shows a bistable multivibrator which senses the return pulse by sampling and feeding back enough phase shifted voltage to re-set the tunnel diodes. Since this device is also dependent upon the return to trigger or re-trigger the parent pulse, it suffers problems with lossy dielectrics and high dielectric constant mediums.

To overcome these problems, the relaxation oscillator of FIG. 4 of Friedman was proposed that contains a RC (resistor/capacitor timing) network which will maintain the generation of pulse trains using resistor 76 and capacitor 78 with the dielectric filled transmission line affecting the regeneration of the pulses as the reflected parent pulse voltage is returned. Since the RC time constant is defining the basic repetition rate, some improvement is obtained in reducing second order effects. The transmission line is still an integral part of the overall relaxation oscillator and lossy dielectrics may cause irregular circuit response. The proposed inverting amplifier as the pulse generator will not function at above approximately 1 MHz in frequency due to the characteristics of such inverting amplifiers. The tunnel diode can pulse up to a 100 MHz rate.

By contrast, the innovative system embodiments disclosed in the present application and its parents differs from the known prior art in using a microwave frequency generated by a free running sine wave oscillator. The preferred oscillator has the versatile capability to work into a wide variety of transmission lines or other load impedance without generation of spurious data or cessation of oscillations. It will continue to oscillate with very lossy dielectrics. It is not a relaxation oscillator or a multivibrator. The frequency of the unisolated oscillator is dependent upon the net complex impedance of the transmission line and will work into an open circuit as well as a short circuit. The net complex impedance at the frequency of operation of the oscillator looking at the transmission line containing the medium of interest results in stable oscillations through pulling of the unisolated oscillator. Only one frequency at any one time is involved in the disclosed system proposed (not counting harmonics which are at least 10 dB down from the fundamental). This provides for well defined information and eases the transmission design criteria. This also provides for evaluation of the dielectric constant versus frequency which can improve resolution of constitutes or ionic activity.

Another important difference from prior art is the separation of the load of interest from the resonant circuit proper. The configuration used isolates the two through the transistor. It is the non-linear behavior of the transistor that provides the changes in frequency as the load is changed. The loop gain of an oscillator must be unity with 180° phase shift. The initial gain of the transistor must be greater before oscillations begin in order for the oscillator to be self starting. This extra gain is reduced to unity by the saturation of the active device upon established of the oscillatory frequency. Saturating a device changes the gain (and accordingly the phase since it is non-linear) to maintain oscillations as the load changes. This will continue as the load changes as long as the transistor has appropriate phase and available gain to satisfy oscillations.

ON-LINE CHARACTERIZATION OF REACTIONS

The disclosed inventions use a load-pull oscillator architecture to directly monitor the changing properties of materials in a process flow. The oscillator load pull technique provides an extremely sensitive measurement of phase changes in a dielectric or semi-conducting medium. Because of the inherent sensitivity of the load-pull oscillator system, it is possible to monitor chemical reactions dynamically. Since most chemical reactions progress through several intermediate states before reaching the final reaction product, it becomes possible to correlate their characteristics to desired properties of the final product. This allows the optimization and control of yield and of product characteristics.[18]

[18] For example, in polymerization reactions, a small change in the reaction conditions may produce a change in product molecular weight (and/or chain length and/or degree of cross-linking) which dramatically changes the mechanical properties of the polymer product.

RELATION OF MEASURED ELECTRICAL PARAMETERS TO MOLECULAR AND MICROSTRUCTURAL CHANGES

The "load pull" technique can reveal very significant information about the chemical and physical organization of the material being studied. Some of the features of interest, and the causative relations between these features and the electrical parameters which are directly measured, will now be described.

TYPES OF POLARIZATION[19]

There are four different mechanisms which can mediate compliance of molecules with an applied electric field: these include electronic polarization, ionic polarizations, orientational, and interfacial polarization. It is important to distinguish these four mechanisms, since they appear to different degrees in different materials, and typically have different strengths and different relaxation-time characteristics.

[19] Maxwell's equations in their full form (as applied to a material body) distinguish the applied electric field vector E from the induced electric field vector D. The two vectors are related as $$D = \epsilon_0 \epsilon E.$$

where $\epsilon$ is a tensor in anisotropic materials, but can usually be treated as a scalar. The induced field D can further be written as the sum of the applied field and a polarization vector P:

$$D = \epsilon_0 E + P.$$

As the following discussion will explain, the polarization vector P can usefully be represented as a sum of four vectors:

$$P = P_{electronic} + P_{ionic} + P_{orientation} + P_{interfacial}$$
$$= P_e + P_{ion} + P_{or} + P_{int}.$$

ELECTRONIC POLARIZATION $P_a$

The electronic polarization $P_{electronic}$ (or $P_a$) represents a shift in the electron cloud of an atom (or molecule) with respect to the nucleus (or nuclei) within the cloud. This polarization has a very short relaxation time, and remains important up through optical frequencies and beyond.

IONIC POLARIZATION $P_{ion}$

The ionic polarization $P_{ionic}$ (or $P_{ion}$) is only found in ionic crystals. It represents displacement of one charged element of the crystal's unit cell with respect to the other elements of the unit cell. This type of polarization has a slower time constant, but remains significant through microwave and submillimeter wavelengths. This type of polarization is responsible for the huge dielectric constants seen at low frequencies in ferroelectric materials such as niobates and titanates.

ORIENTATIONAL POLARIZATION $P_{or}$

Orientational polarization $P_{orientation}$ (or $P_{or}$) occurs when individual molecules of a substance have separate dipole moments (on a small scale). (Many substances have such atomic dipole moments.) In such substances, an applied electric field will tend to orient the molecular dipoles.[20] This mode of polarization is still slower, with a relaxation time which is typically on the order of microseconds (so the cutoff frequency is typically well below 1 MHz).

[20] An extreme example of such orientation is the practice of "poling" electrets, in which large molecules including charged groups are frozen into a polarized condition by applying an electric field.

A related phenomenon, on a much slower time scale, can occur in two-phase compositions. For example, where aspherical solid grains are dispersed in a fluid medium with a lower dielectric constant, the solid grains will tend to orient along the electric field lines.

INTERFACIAL POLARIZATION $P_{int}$

Classically, interfacial polarization $P_{interfacial}$ (or $P_{int}$) occurs in solids when charged carriers migrate to a grain boundary (or defect site, etc.). This can be the slowest of all the polarization mechanisms described, with a time constant (determined by the rate of diffusion of carriers) of the order of seconds.

A related phenomenon can also occur in two-phase compositions. For example, where small metallic grains, or droplets of salt water, are dispersed in oil, charge separation may occur across each conductive element. Where in resistivity of the conducting domains is low, the cutoff frequency in such cases may be high enough to be of interest in fluid measurement systems.

CHEMICAL AND MICROSTRUCTURAL DIFFERENCES CONDUCTIVE TO ANALYSIS

The disclosed techniques and system embodiments can accordingly be used to monitor substances and reactions in many ways, by making use of many different effects.

INCREASED MOLECULAR POLARIZATION

Increased polarization of the molecule will provide a higher dielectric constant, and thereby cause a frequency shift.

INCREASED ORIENTATIONAL POLARIZATION

This too will tend to increase the dielectric constant. Orientational polarization will typically be quite lossy at RF frequencies.

INCREASED INTERFACIAL POLARIZATION

This too will tend to increase the dielectric constant, and will typically be quite lossy at RF frequencies.

INCREASED IONIC POLARIZATION

Increased ionic polarization of the molecules can happen, for example, as a result of a reaction which transfers charged functional groups. This will lead to a shift in dielectric constant and distinct change in microwave loss characteristics.

POLARIZATION DEPENDENCE ON BOND SHIFTS

Bond positional changes cause a shift in dielectric constant due to the change in polar moment.

Moreover, the change in the interstital fit of a sea of molecules due to a shift in the bond locations can also cause a density change which, in turn, causes a shift in dielectric constant. This can also lead to a shift from non-ionic to ionic structures.

RELOCATION OF FUNCTIONAL GROUPS

Group site changes will tend to have an effect which is at least as strong as bond shifts. Moreover, if a molecular resonant frequency can be sampled, a strongly detectable difference may be found.

INCREASED CHAIN LENGTH

Growth of the molecule (by adding more chains, even without an associated ionic change) will cause a shift in density and, therefore, dielectric constant. This will also shift any rotational or vibrational resonances of the molecule to a lower frequency.

CHANGES IN IONIC BONDING CHARACTER

Changes in the degree of ionicity of bonds, or changes from non-ionic to ionic bonding, are easy to detect. These changes will affect the insertion loss at microwave frequencies the greatest.

MOLECULAR RESONANCES (ROTATIONAL AND VIBRATIONAL)

Molecular resonance will be seen at specific microwave frequencies as a dip in power and a change (not unlike injection locking an oscillator) in frequency due to the changing load effect of the resonance.

PARTICULATE CONTAMINATION

Particulate contamination (e.g. by metal particles) will be seen as a shift in frequency with little change in power due to the small size of most contaminants. The metal particles described are seen as an artificial dielectric, due to the small areas and the effect of the interfacial polarization. This will increase the dielectric constant.

DILUTION/ADDITION

Changing the molar content of a solution will adjust the dielectric constant and ionic strength accordingly, and will shift the microwave frequency and the power, respectively.

MOLECULAR RECOMBINATION

Of course, the formation of different compounds will alter the characteristics of the dielectric constant and the loss.

USE OF "TAG" COMPOUNDS TO TRACK REACTIONS

In addition to direct monitoring of reactions, monitoring can be enhanced by adding a "tag" compound into one of the ingredients. Such tagged compounds can be used to track reactions which would not otherwise have a great enough microwave response. The "tag" compounds would attach before, during, or after the chemical process has occurred, but they would not alter the reaction product. They would increase the "visibility" of the process to the microwave system.

FINE STRUCTURE OF DISPERSIONS

The dielectric constant of a sol or a two-phase mixture will have a direct correlation to the degree of dispersion.

GROUPING ABOVE THE MOLECULAR SIZE RANGE

The short-range ordering of molecules such as polywater or thixotropic substances will show different microwave properties due to the "sea" of molecules' polar moment changing relative to the state of polarization or linkage. This will be reflected in the microwave system as a change in dielectric constant.

PHASE CHANGES

Phase changes of materials can be seen due to the change in dielectric constant. This can include introduction of a gas phase or a phase change such as oil continuous phase (droplets of oil surrounded by water as the continuous medium).

CONDUCTIVITY CHANGES

Changes in the conductivity of a material are likely to produce a strong shift in the electrical characteristics, for several reasons. First, increased conductivity will typically increase the RF loss, since free carriers are subject to loss mechanisms which do not apply to orbital shifts. Second, the presence of additional free carriers can increase the contribution of interfacial polarization, in a two-phase medium, if the frequency is low enough to let this become important.

MEASUREMENT OF MULTIPLE PARAMETERS

The load-pull oscillator architecture permits direct measurement of a number of parameters, including:
1. Oscillator frequency shift.
2. Insertion loss.
3. Both oscillator frequency shift and insertion loss will vary with frequency, in ways which vary from one substance to another.
4. Both oscillator frequency shift and insertion loss will vary with temperature, in ways which vary from one substance to another.
5. Oscillator frequency and/or insertion loss may vary usefully with pH, or with the some other concentration value, so that the oscillator's behavior can be tracked during a short titration process to gain additional information.

Although signal attenuation will be the aggregate response of all contributing components, a variety of system information may be derived directly or indirectly from the direct measurements. Some of the more important ones are:
(A) reaction kinetics (reaction rate) and extent of reaction.
(B) ratio of desired compounds in final product to that produced by a competing side reaction.
(C) physical phase changes in reaction vessel.
(D) reactions reflecting the condition of the catalyst.

EXAMPLE

If a non-ionic solution is reacted producing an ionic solution, this will cause power loss in the medium to increase due to the increased conduction in the microwave section. The slope measured at two widely separated frequencies will be vastly changed, since this is a very frequency dependent loss. An associated frequency change will be seen in the oscillator since the frequency change will be seen in the oscillator since the frequency of oscillation is dependant upon the resultant complex impedance (real and imaginary parts of the impedance).

EXAMPLE

If the reaction only contains substances that during the reaction create bond position changes or re-orientation of bond groups (non-ionic exchanges or large shifts in pH), this may require a higher frequency to discern the chemical changes. Loss will not be appreciable unless the frequency is high enough to observe structure resonances (polar resonances). Widely separated tuning voltages on a given VCO will give frequency differences which are unique (due to varying dielectric properties versus frequency). A broadband sweep and the resulting location of frequency hops will indicate relative dielectric constant as well as indications of dielectric change versus frequency. Frequency hops are caused by the oscillator seeing a phase shift going from inductive to capacitive or vice versa. This creates frequency discontinuities of approximately 20 to 60 MHz (dependant upon the magnitude of the real part and the fundamental frequency of operation) when the load traverses this point in the complex plane.

EXAMPLE

If the reaction has properties of progressing through various sub-classifications of reaction type, each change (from ionic to non-ionic to bond changes for example) will have changing slopes of frequency versus time and frequency versus power loss. The differentiated functions will give indication of the progress of the reaction. Further knowledge of the constituents may be discerned through the voltage sweep of the Voltage Controlled Oscillator to reveal the frequency hop positions.

EXAMPLE

If more specific knowledge of the chemical constituents is required, high frequencies may be used to look at the apparent microwave resonance caused by the molecular resonance. This apparently begins to occur at wavelengths of frequencies above 9 GHz. Using the oscillator load pull technique, the molecular resonance will appear as a type of frequency hop as the VCO is tuned through its tuning voltages. The effect will be similar to that of injection locking of an oscillator. This will occur due to the sharp loss of the medium on each side of the center frequency loading the oscillator though the frequency span of the resonance; therefore, the oscillator will stop tuning as the tuning voltage increase or decreases about the point in frequency that the molecular resonance occurs.

Due to the sensitivity of the load pull technique, low frequencies will give good results even for minute changes in pH or bonding position. This provides the ability to make full stream process measurements without sampling, due to the long wavelengths at the present operation frequency of 200 MHz to 1 GHz. The coaxial section which is presently used will propagate in one mode and therefore does not further complex the data.

The molecular resonance quasi-injection lock phenomena will require small cross section measurements (0.5 inch diameter cross-section pipe) to prevent these mode shift problems. Once again, this is due to the small wavelengths involved that will reveal molecular resonance.

THE NEED FOR REAL TIME MONITORING OF ORGANIC REACTIONS

The apparatus and techniques used in organic chemistry differ from those used in the inorganic field. There are at least two general differences which affect the chemical engineering needed:

1) The reactions of organic compounds are characteristically much slower than inorganic reactions. Thus, elevated temperatures and long reaction periods are the rule in organic chemistry, necessitating the use of reflex condensers, autoclaves, stirring devices, and similar equipment not ordinarily required in inorganic synthesis.

2) Inorganic reactions are typically "quantitative," i.e. they react completely to produce a single stoichiometric compound. In distinct contrast, such a *quantitative* reaction is exceptionally rare among organic reactions. Yield of 80%-90% of the theoretical are regarded excellent, yields of 50% are often acceptable, and frequently the chemical industry must be satisfied with yields of 20%-30%.[21]

[21] The remainder is undesired compound(s), and is either tolerated or separated off by a subsequent procedure (such as solvent extraction or fractional distillation), which adds cost.

There are two principal reasons for the nonquantitative nature of organic reactions. First, very few species of organic matter are capable of undergoing only *one* reaction under a given set of experimental conditions. Side reactions almost invariably occur. The second factor limiting the yields obtained from organic reactions is the reversibility of the reactions.[22] Such reversibility places a definite limit on the yield of a product obtainable under any given set of experimental conditions.

[22] Organic reactions are often driven by relatively small differences in thermodynamic potential, and this causes the reactions to be less irreversible.

Many competing factors can affect yield (total amount produced) and purity (degree of contamination by side reactions). For a chemical refinery, improved yield and purity both translate directly into higher gross income. Thus, an immense amount of effort has been devoted to optimization of chemical engineering systems to increase yield and purity. In particular, a very large amount of effort has been invested in developing automatic control strategies.[23] However, one constraint on control strategies in chemical engineering has been that real time data collection was quite limited (primarily to temperature, pressure, and mass flows), and analyses of chemical composition has to be done off-line.

[23] Some patent literature which appears to show the status of process control architecture in various segments of the chemical and related industries, includes U.S. Pat. Nos. 4,844,856 ("Process for automatic regulation of the soluble boron content of the cooling water of a pressurized water nuclear reactor"); 4,744,408 ("Temperature control method and apparatus"); 4,713,774 ("Alkylation reactor quality control"); 4,688,726 ("Method and apparatus for controlling a particle refining process"); 4,600,570 ("Continuous controlled process for removing sulphur oxides gases from stack gases"); 4,438,499 ("Fractional distillation process control"); and 4,399,100 ("Automatic process control system and method for curing polymeric materials"). composition, since they are produced in a similarly ill-controlled fashion. Secondly, the reaction system normally consists of a series of connected chambers or zones in which parameters such as temperature are manually set. If for any reason a chemical system imbalance occurs as a phase change, this disturbance can propagate down the system undetected and without compensation.

PROCESS CONTROL ARCHITECTURES WITHIN THE CHEMICAL INDUSTRY

The use of closed loop control systems, in which compositional characteristics are interactively related to process parameters, is still not widespread in the chemical industry.[24] This seems to be due to the following reasons:

1. The industry is mature and capital-intensive, using equipment designed and built a decade or so ago. Operating procedures (as in the petroleum industry) tend to be highly formalized in practice and philosophy.
2. The improved types of equipment which could be used for monitoring are typically expensive, intended for laboratory use, and not easily converted for use in a harsh refinery type of environment. For example, chromatographs have found some usage, but are slow (response time of 5 to 20 minutes), easily contaminated, and difficult to use with high melting point materials as polymers.

[24] Of course, many systems use programmable controllers whose inputs (measured variables) are non-compositional variables, such as temperature, pressure, mass flows, and integrals of derivatives of these.

Historically, the economic benefits of process yield improvement were not a primary focus of effort in applied chemical engineering. The chemical industry was founded in the days of cheap oil and cheap energy. Most of the current manufacturing facilities date from that period. The low usage of instrumentation for real time control stems from the attitude that "what we already have does the job". Only during the last few years has attention been directed toward this area.

An example of recent activity is an article describing the installation of gas chromatograph for "real time"[25] control of a distillation tower. Bozenhardt, "Modern Control Tricks solve distillation problems," *Hydrocarbon Processing*, Jun. 1988, at 47, which is hereby incorporated by reference. This installation used a $150,000 gas chromatograph, plus about $200,000 for instrumentation and control system. During a twelve month period, this saved the refinery operator $3,000,000 in energy consumption *alone*, in addition to stabilizing the yield (which otherwise would drift as low as 82%) at 95%. This 13% yield swing represents 39 million pounds of lost product revenue on an annual basis. Prior to this conversion, no economic significance has been assigned to it because this performance was previously believed unachievable.

[25] This was not "real time" by electrical engineering standards, since the entire system has a "dead time" of almost 20 minutes.

BRIEF DESCRIPTION OF THE DRAWING

The present invention will be described with reference to the accompanying drawings, which are incorporating in the specification hereof by reference, wherein:

FIG. 12A shows the reaction pathways in reacting maleic anhydride with isoprene.

FIG. 12B schematically shows the change in oscillator frequency when maleic anhydride is added to benzene, and isoprene is added thereafter.

FIG. 12C schematically shows the change in oscillator frequency with temperature for the reaction products of the reaction of FIG. 12B.

FIG. 12D schematically shows the change in oscillator frequency when isoprene is added to benzene, and maleic anhydride is added thereafter.

FIG. 16A shows the temperature dependence of oscillator frequency, with the system loaded with formic acid in benzene.

FIG. 16B shows the temperature dependence of oscillator frequency for chlorobenzene.

FIG. 16C shows the temperature dependence of oscillator frequency for cyclohexane.

FIG. 16D shows the temperature dependence of oscillator frequency, with deionized water in the system.

DESCRIPTION OF THE PREFERRED EMBODIMENTS

The numerous innovative teachings of the present application will be described with particular reference to the presently preferred embodiment, wherein these innovative teachings have been demonstrated in a wide variety of reactions (primarily organic). However, it should be understood that these embodiments provides only a few examples of the many advantageous uses of the innovative teachings herein. In general, statements made in the specification of the present application do not necessarily delimit any of the various claimed inventions. Moreover, some statements may apply to some inventive features but not to others.

SAMPLE SYSTEM CONFIGURATION

A first sample system configuration, as set forth in the grandparent application, will now be described. This system was optimized for monitoring the characteristics of a high-volume fluid flow, namely unrefined petroleum. Other system embodiments will be described below.

Figure 1:
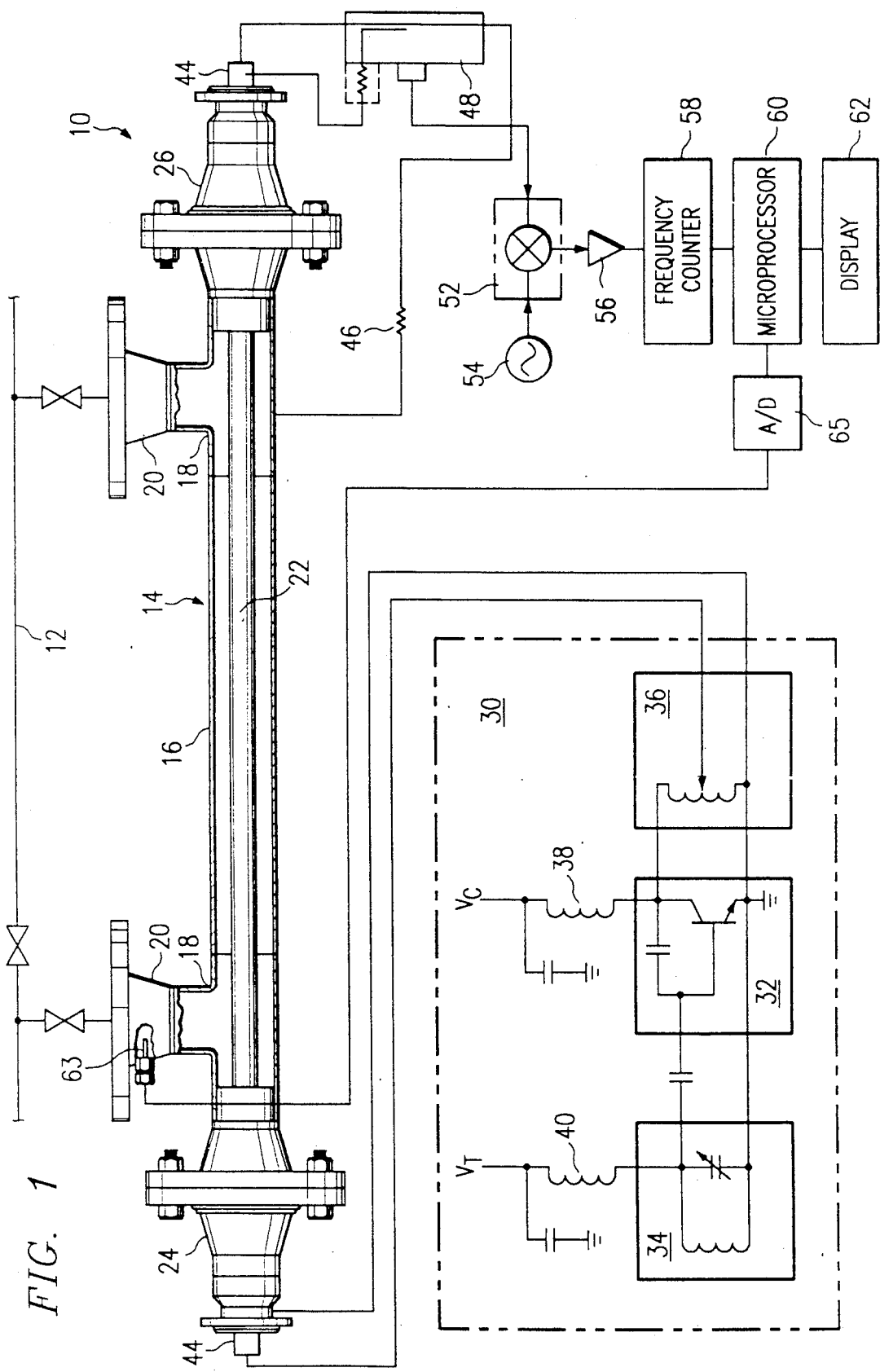
FIG. 1 is a schematic diagram of a first apparatus embodiment as disclosed in the grandparent application.

Referring to FIG. 1, an apparatus for measuring the concentration of a liquid in a liquid flow stream is illustrated, and is generally designated by the numeral 10. The apparatus 10 is particularly adapted for interconnection with a fluid transmission pipeline 12 for sampling the flow stream through the pipeline or by actually becoming interposed as a part of the pipeline. The apparatus 10 includes a fluid flow conducting and measurement section 14 comprising a conventional outer conduit section 16, spaced apart "T" sections 18, and conventional weldneck pipe flanges 20. The liquid mixture to be measured for determining the concentration of one medium in the other may be conducted through the conduit 16 on a continuous basis, and the measurement section 14 may comprise part of a fluid transmission pipeline. An elongated center conductor 22 extends through the conduit 16 between opposed support end parts 24 and 26, which will be described in further detail herein in conjunction with FIG. 2. The center conductor 22 may comprise a generally cylindrical rod member or tube member and is preferably coaxially arranged in the conduit 16, including the opposed end or "T" section 18. The measurement section 14 can be configured to contain a quantity of fluid or other compositions of matter without continuous or intermittent flow through the measurement section for use of the apparatus in laboratory sampling procedures, for example.

The apparatus measurement section 14 is operably connected to a source of radio frequency or so-called microwave energy comprising an unbuffered or unisolated oscillator, generally designated by the numeral 30. The oscillator 30 includes an active circuit 32 operably connected to a tuning circuit 34 and to an impedance matching network circuit 36. (It has been discovered that a system as shown in FIG. 1 can be operated without the impedance-matching network, and this is preferable. In further embodiments, if the measurement section 14 may see a very wide range of dielectric constants, a PIN-diode-switch can be used to switch in circuit elements for impedance matching as needed.) The active circuit 32 is adapted to receive a constant DC voltage, $V_c$, from a source, not shown, by way of a filter circuit 38, and the tuning circuit 34 is adapted to receive a controllable DC voltage, $V_T$, in the presently preferred embodiment, from another source, not shown, by way of a second filter circuit 40. An unbuffered oscillator such as the oscillator 30 has an appreciable load pulling characteristic. The fundamental operating frequency of the oscillator is changed as the complex load is changed on the output circuit of the oscillator. Depending on the coupling factor of the output circuit the load pulling characteristic can be negligible or substantial. Increasing load pulling factor increases the possibility of so-called spectral breakup (multiple frequency operation) which would render the desired measurement of the oscillator signal impossible. The oscillator 30 may be of a type commercially available, such as from the Watkins-Johnson Company, Scotts Valley, Calif., as their Model D-827 voltage controlled oscillator. The exemplary oscillator 30 has a maximum load pulling characteristic of about 35 MHz at a nominal 1.60 GHz operating frequency into all phases of a short circuit at the end of a 50 ohm line stretcher (approximately 0.5 dB return loss). If such a line was of constant loss versus phase, the frequency of the oscillator would return to its original frequency, at any particular phase, every time the reflection co-efficient at that phase recurred with an augmentation of n360°.

The oscillator 30 is operably connected to the apparatus measurement section 14 through a suitable connector 44 which is in electrically conductive engagement with the center conductor 22 at the end part 24. At the other end of the load cavity, the center conductor 22 is also electrically connected, through end part 26, second connector 44, and resistance 46, back to the outer conductor 16, as illustrated. (In the presently preferred version of the system of FIG. 1, the resistor 46 is simply replaced by a short circuit. However, various other load elements could be used instead, including real, complex, or frequency-dependent impedances.) The end part 26 is also adapted to interconnect the center conductor 22 with a ten dB directional coupler 48 which is operable to sample the energy transmitted through the coaxial measurement section 14. (Of course, the coupler 48 could also be placed elsewhere in the circuit.)

Now consider the electrical behavior of the system of FIG. 1 as a varying oil/water mixture flows through the conduit 16. As the percentage of water in this mixture changes, the dielectric constant of the mixture will change. Therefore, the complex impedance characteristics of the measurement section 14 change too. Therefore, the operating frequency of the oscillator 30 will also change. The amplitude of the signal seen at mixer 52 will also vary as the concentration of water varies. However, the frequency characteristic provides for more accurate measurements.

The coupler 48 is connected to a receiver system which includes a mixer 52 and an isolated oscillator 54 which is tuned to provide a differential output signal. The differential output signal is amplified by amplifier 56, and its frequency is measured by frequency counter 58. The counter 58 is operably connected to a microprocessor 60, which in turn is suitably connected to a display or readout device 62. The mixer 52 may also be of a type commercially available from the Watkins-Johnson Company as their Model WJ-M7B. The amplifier 56 is also available from the abovementioned company as their Model WJ-A38. The frequency counter 58 may be of a type manufactured by Hewlett-Packard as their Model 5342A and the microprocessor 60 may also be of a type manufactured by Hewlett-Packard as their Model 9836. The receiver system described above may also be modified to include a signal amplitude detector, not shown. The system illustrated in the drawing figures preferably comprises means for compensating for the temperature of the medium being measured in the measurement section 14, including a thermocouple 63 interposed in the flow path of the medium. The thermocouple 63 is suitably connected to a conversion circuit 65 to provide a suitable digital signal to the microprocessor 60 related to the temperature of the medium being measured.

In this example, the changing dielectric constant of the fluid in measurement section 14 causes the oscillator 30 to change its operating frequency over a relatively narrow frequency band as compared with the nominal operating frequency of the oscillator. The oscillator 30, in this example, can be pulled from its nominal operating frequency through a range of about 20 MHz by the changing dielectric constant of the medium flowing through the measurement section 14 wherein the percentage of water in oil, for example, varies over a range of approximately zero to two percent of the total fluid volume. The sensitivity of the oscillator 30 to the change in the water content of the oil/water mixture is particularly high due to the operating frequency of the oscillator since the phase change of the relatively high frequency signal is magnified to some extent by the decreased wavelength at these frequencies and the length of the measurement section 14 is multiple wavelengths. A corresponding increase in sensitivity of the system 10 can also be obtained (for a given starting frequency of oscillator 30) by increasing the length of the measurement section 14.

By sweeping the oscillator operating frequency across a frequency span of approximately 400 HMz (by varying the tuning voltage $V_T$ which is applied to the varactor in the resonant tuning circuit 34), the sensitivity of the operating frequency for a particular tuned frequency may be determined.

As noted, in the embodiment of FIG. 1, local oscillator 54 and mixer 52 provide a differential, relatively low frequency output to frequency counter 58. (However, in the presently preferred version of the system of FIG. 1 downconversion is *not* used, and the frequency counter 58 directly counts the frequency of oscillation.) The frequency counted by the counter 58 may be compared with frequency data stored in the microprocessor 60 and corresponding to a range of percentages of one medium in another such as water in oil. The value thus found is then suitably converted to drive a display 62, which thus displays the amount of or concentration of one medium in the other. The frequency counter 58 may include suitable analog to digital conversion devices, not shown.

As noted, the oscillator 30 has only a limited range of steady frequency deviation. If the load characteristics steadily change enough to pull the oscillator 30 beyond its limited range, the oscillation frequency will suddenly change discontinuously, or "hop."

Accordingly, measurement can be made over a broader range, by making an additional measurement to determine which range the system is operating in. For example, in combination with a system 10 as shown in FIG. 1, a crude measurement can be made to ascertain whether the system is perceiving a concentration of a medium such as water in oil in the range of say zero to two percent or in a range of two percent to four percent (wherein each two percent change corresponds to the full frequency range of operation of the oscillator).

Figure 3:
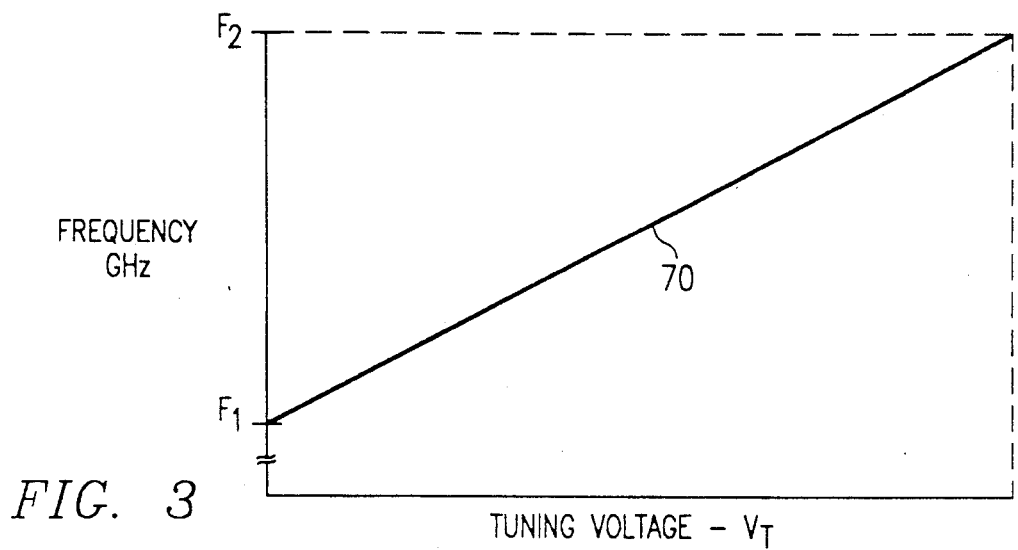
FIGS. 3 through 5 are diagrams showing the frequency characteristic versus the tuning circuit voltage of the unisolated oscillator of FIG. 1, for its full range of frequencies under loads corresponding to certain concentrations of one liquid such as water in another liquid such as oil.
Figure 4:
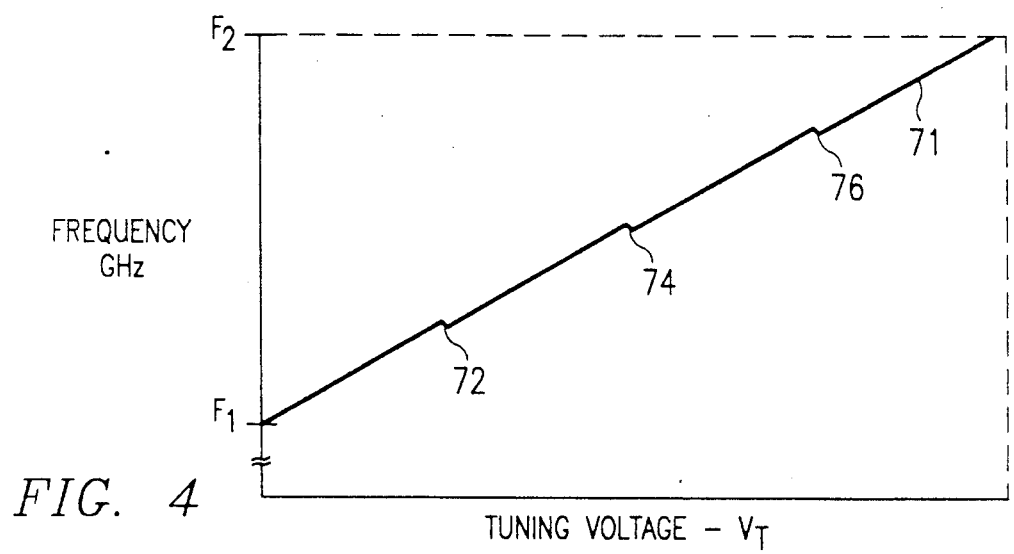
Figure 5:
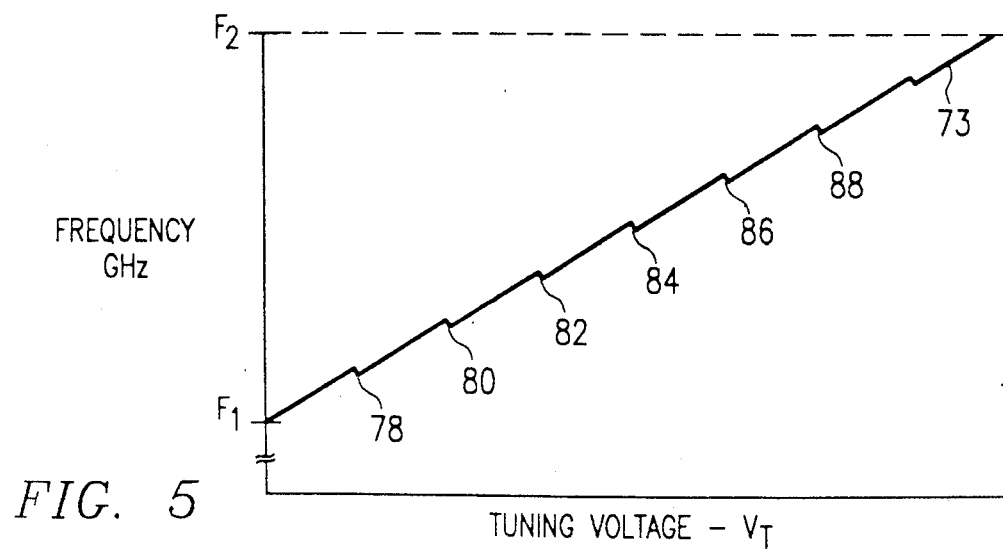

Referring now to FIG. 3, there is illustrated a diagram showing the variation in the output signal frequency of the oscillator 30 over its maximum tunable frequency range when tuned by the tuning circuit 34 when the circuit is terminated into its characteristic impedance. A voltage controlled oscillator such as the oscillator 30, when swept across its maximum range as determined by changing the tuning voltage $V_T$, will exhibit a characteristic indicated by the line 70 for a perfect or balanced load. If the dielectric constant of the composition present between the conductors 16 and 22 changes (e.g. as a result of a change in the concentration of one medium, such as water, in another medium, such as oil, over concentrations in the range of zero to two percent), the oscillator 30 will exhibit a frequency output signal as shown in FIG. 4. A curve 71 having discontinuities 72, 74, and 76, will be exhibited as the oscillator 30 is swept across its maximum frequency range. Accordingly, as the oscillator is swept across its maximum frequency range (indicated as $f_1$ to $f_2$), the number of discontinuities may be counted to determine what range of change in concentration of water in oil, for example, is being measured. For example, as shown in FIG. 5, a curve 73 having discontinuities indicated by the shifts 78, 80, 82, 84, 86, 88, and so on, would indicate that the oscillator 30 was measuring a change in frequency for a concentration of water in oil of say two percent to four percent. Therefore, the number of discontinuities measured per sweep of operating frequencies from $f_1$ to $f_2$ can indicate what range of variation in dielectric constant is being measured which correlates with the range of concentration of one medium such as water in the other medium such as oil.

Accordingly, by using an unisolated or unbuffered voltage controlled oscillator in a circuit such as described herein, an operating frequency at a particular control voltage may indicate the concentration of water in oil, for example, if after sweeping the oscillator across its frequency range, the number of 360° phase shifts counted are determined to determine the particular range of change of dielectric constant being experienced.

Figure 6:
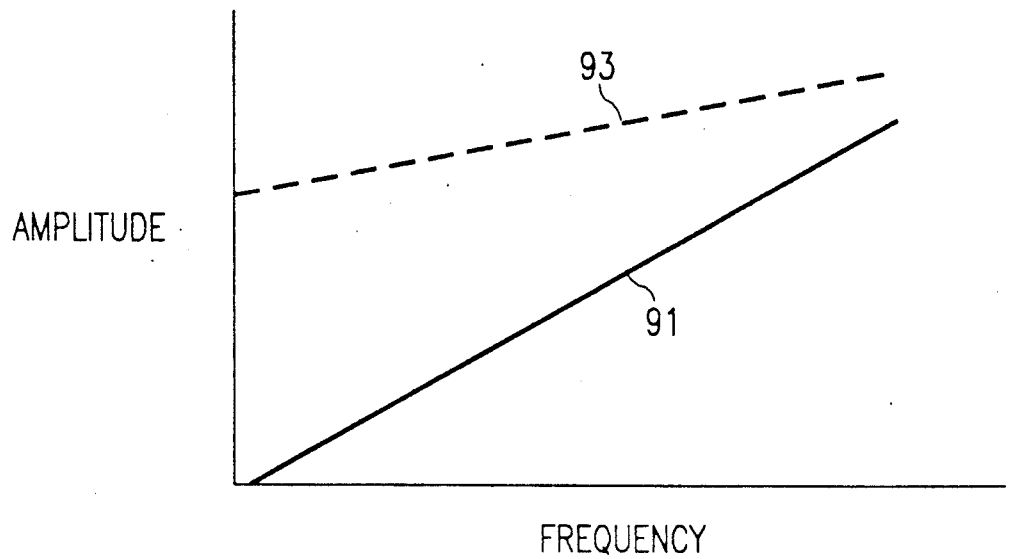
FIG. 6 is a diagram illustrating the effect of salinity of water in an oil-water mixture when measured by the apparatus FIG. 1.
Figure 7:
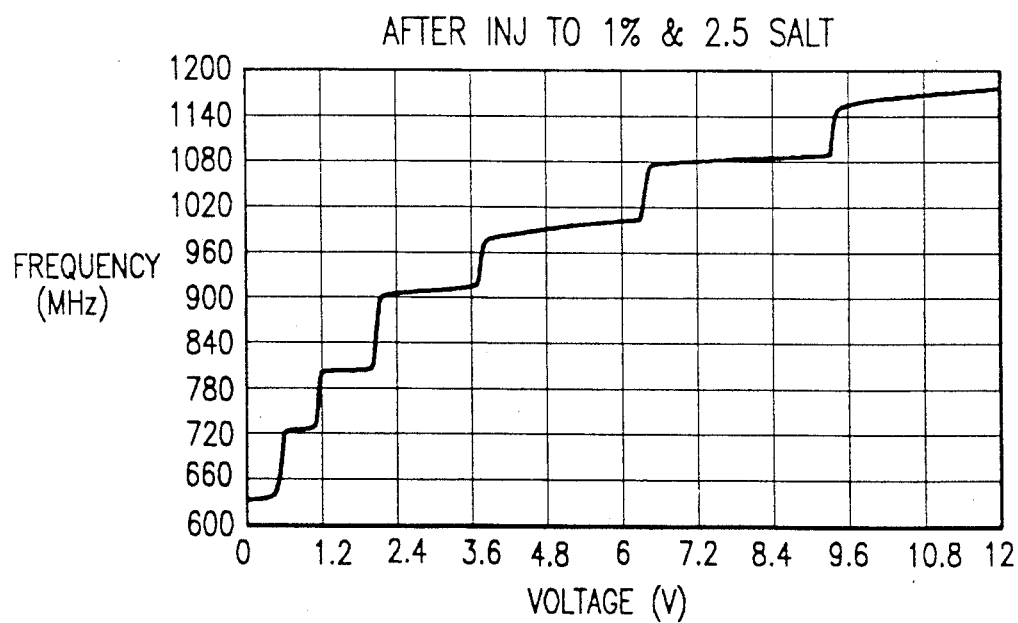
FIG. 7 shows a typical tuning frequency versus voltage plot for a VCO loaded into a shorted transmission line.

Referring now to FIG. 6, there is illustrated a diagram indicating the relationship between the oscillator signal frequency and amplitude and the effects of the salinity of a medium being measured, such as an oil-water mixture. The measurement of signal amplitude at several frequencies and a knowledge of the effect of salinity on the intercept of the frequency characteristic as a function of amplitude can correct for salinity effects on the overall impedance seen by the oscillator 30. For example, a salt-free fluid with a particular percentage of water in oil will exhibit a signal characteristic according to the curve 91 in FIG. 6, whereas the same percentage of water in a water-oil mixture with, for example, y molar percent of sodium chloride would exhibit a characteristic according to the curve 93 in FIG. 6. Thus, by sweeping the frequency of the oscillator 30 across a range of frequencies, the salinity, as well as the percentage of water, can be measured.

Figure 2:
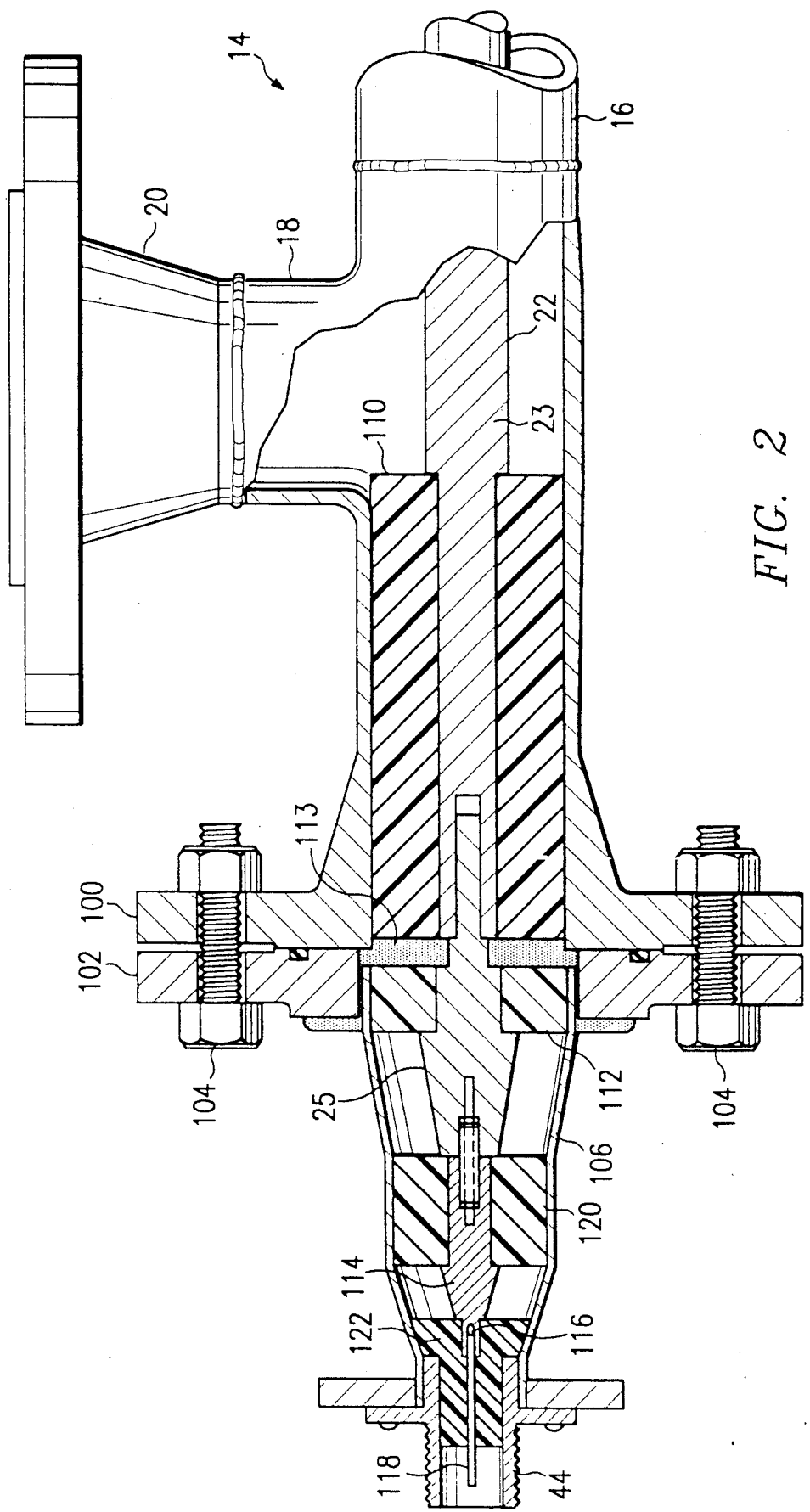
FIG. 2 is a section view of a portion of the combination coaxial waveguide or transmission line and fluid measurement section of the apparatus of FIG. 1.

Referring now to FIG. 2, there is illustrated a sample arrangement of supporting the center conductor 22 within the measurement section 14 and terminating the center conductor at the conventional N type RF connector 44.[26] (The arrangements for terminating the conductor 22 at the two end parts 24 and 26 are essentially identical. Each of the conduit "T" section 18 is suitably welded to a conventional weldneck flange 100, as illustrated by way of example in FIG. 2, which in turn is secured to a flange 102 by conventional bolt and nut assemblies 104. The flange 102 is secured to a somewhat conical shaped reducer section 106. The internal space formed within the "T" section 18 and the weldneck flange 100 is occupied by a generally cylindrical block 110 formed of a suitable insulating material such as a fluorocarbon plastic.

[26]In the invention as presently practiced, the arrangement of FIG. 2 has now been considerably simplified. O-rings are now included in piece 110, and epoxy cementing is not needed.

The center conductor 22 includes a generally cylindrical rod-like section 23 which is suitably supported in the block 110 and is in conductive relationship with a somewhat frustoconical conductor section 25 supported in a second support block 112 formed of an electrical insulating material. The conductor section 25 is secured to a third conductor section 114 by a conductive pin member 115. The conductor section 114 also has a somewhat frustoconical or tapered portion for reducing the diameter of the center conductor down to a portion 116 which is secured to a pin 118. The pin 118 comprises the center conductor for the connector 44. The conical tapered conductor sections 25 and 114 also prevent unwanted reflections of the signal being transmitted through the measurement section 14. Suitable insulating bushings or spacers 120 and 122 are adapted to support the conductor sections 25, 114, 116 and 118. A suitable insulating material and sealing, such as epoxy, may be injected to fill the cavity formed between the blocks 110 and 112, as indicated at 113, to prevent leakage of fluid from the interior of the conduit section 16 to the opposite ends of the measurement section 14. Thanks to the configuration of the end parts 24 and 26, there is little or no space provided which would create a void of non-flowing fluid within the measurement section 14 which might introduce errors into the determination of the concentration of one fluid in another being pumped through the measurement section. The "T" sections 18 might be replaced by conduit portions which would introduce flow into the conduit section 16 with a more gradual change of direction to minimize turbulence which could possibly affect the frequency readings being measured by the circuit described herein.

ACQUIRING DATA FROM CHEMICAL REACTION IN PROGRESS

The sample system used for the successful experiments summarized in FIGS. 11-23 will now be described in detail.

PHYSICAL CONFIGURATION AND FLUID FLOWS

Figure 8:
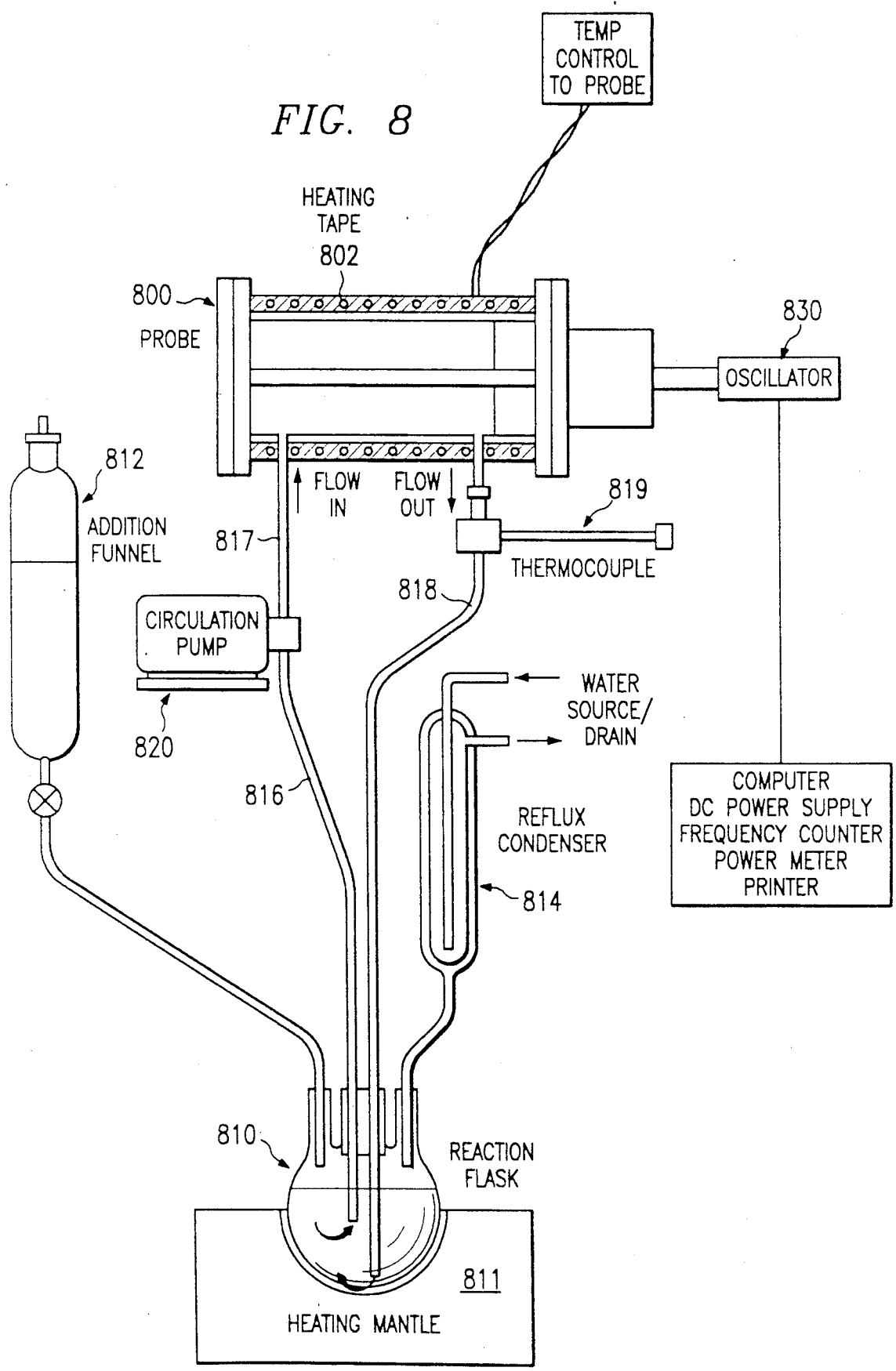
FIG. 8 shows the physical configuration actually used to derive the data of FIGS. 11-20.

FIG. 8 shows the physical configuration actually used to derive the data of FIGS. 11-23.

A reaction flask 810 is fed by an addition funnel 812, and is also connected to a reflux condenser 814. (The reflux condenser 814 is watercooled, and helps to prevent the loss of volatile fractions from the system.) The temperature of the reaction flask is stabilized by a heating mantle 811, which preferably is actively heated and has a large thermal mass. The heating mantle 811 is normally controlled to maintain a constant temperature in the reaction flask 810.

A circulation pump 820 pumps liquid out of the flask 810 (through tubing 816), into measurement section 800 (through tubing 817), and back into the reaction flask 810 (through tubing 818).

Thus, the composition of the material in the measurement section 800 will correspond to the composition of the material in the flask 810. To preserve uniform temperature, a heating tape 802 is attached to the measurement section 800, and is controlled in accordance with the output of thermocouple 819 to keep the temperature of the fluid approximately uniform throughout the system.

The measurement section 800 is physically shaped as a cylindrical cavity with an insulated probe rod along the axis of the cylinder. This is electrically connected to an oscillator network 830, as will now be described.

ELECTRICAL CONFIGURATION

Figure 9:
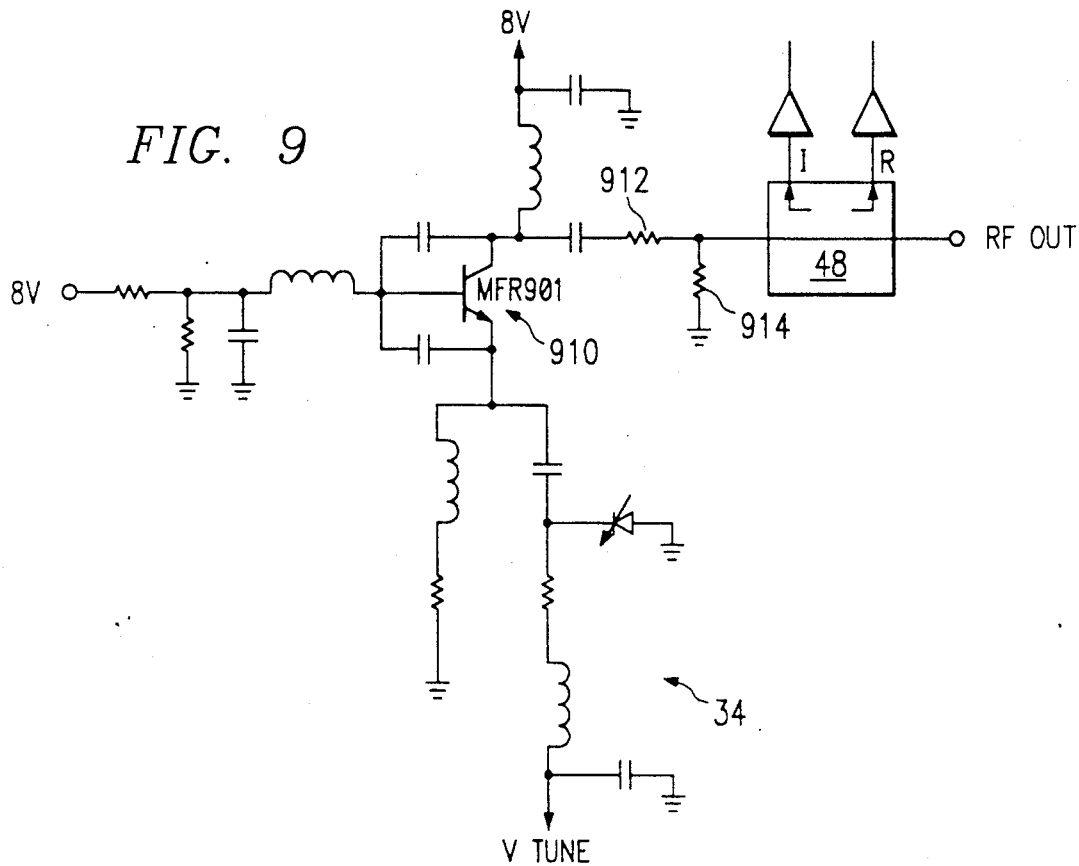
FIG. 9 shows the electrical configuration used, with the physical configuration of FIG. 8, to derive the data of FIGS. 11-23.

FIG. 9 shows the oscillator configuration used, with the physical configuration of FIG. 8, to derive the data of FIGS. 11-23.

Note that his configuration has some differences from the configuration of FIG. 1. The load seen at line RFOUT (presented by the measurement section 800) is connected to the collector of driver transistor 910, while the tank circuit 34 is connected into the emitter-base coupling of driver transistor 910. The directional coupler 48 is now a dual directional coupler which is connected directly to the line RFOUT, instead of being separated by the length of the measurement section 14, as in the embodiment of FIG. 1.

Note that a small series resistor 912 is used in the RFOUT line. (In the presently preferred embodiment, the value of this component is 9Ω). This resistor helps to prevent spectral breakup (by suppressing oscillation at secondary frequencies).

A shunt resistor 914 is also attached to the RFOUT line. This resistor also adds to stability, by fixing a maximum magnitude for the impedance seen at line RFOUT. (In the presently preferred embodiment, the value of this component is 562Ω.)

These two resistors will reduce the magnitude of the frequency hops seen, as discussed above.

The directional coupler preferably diverts only 1% of the reflected power, so that the load is still coupled closely enough to be able to pull the oscillator. The corresponding output from coupler 48 is connected to a frequency counter and control logic, as described above. Also, the two outputs from the directional coupler are used to measure inserted power and reflected power.

EXPERIMENTAL DATA FROM REACTION MONITORING

FIGS. 11-23 show the results of a number of experiments which have demonstrated the ability of the disclosed system to monitor the progress of a wide variety of chemical reactions. In these experimental runs, the data was gathered with a system substantially as shown in FIG. 8.

In the measurement system used, the frequency was read out to a resolution of 100 Hz. When the system pump is operating, the 100-Hz digit of frequency measurement displays some rapid fluctuation, due to bubbles in the system, but the 1000-Hz digit of the frequency measurement is stable.[27] The insertion loss measurements are read out to a resolution of 0.01 dB. Again, some fluctuation was seen in the 0.01 dB digit, but the 0.1 dB digit is quite stable. Thus, in the following results, frequency measurements are reported to a resolution of only 1000 Hz, and the insertion loss measurements are reported to a resolution of 0.1 dB.

[27]With pump off, the frequency readout is stable down to about 10 Hertz.

In the system used, the volume of the measurement section was 0.5 l (of a total volume of 1.5 l), and the pump flow was 4l/min. Thus, the time delay to replace the volume of the measurement cavity is 0.5/4 min = 7.5 sec. This physical time constant limits the time-domain resolution of all measurements given (except for pressure-dependent behavior, as in run 19 below). Note that significant information can be seen on a much smaller time scale, but such information may be regarded as an average over a time window of about 7.5 seconds. Note that the electrical time-domain resolution limits are of the order of $1/f$, i.e. roughly a few nanoseconds.

TABLE OF PERMITTIVITIES

To assist those skilled in the art in interpreting and extrapolating from the following results, the following table gives DC permittivity values $\epsilon_r$ for several of the substances described below. The permittivities at UHF and microwave will be somewhat different from the DC values, but the DC values do show the low-frequency component of permittivity. Unless otherwise specified, the following values are for the pure substance, in liquid or solid form, at room temperature and atmospheric pressure.

| | |
|---|---|
| Aniline: | 6.89 |
| Benzene: | 2.28 |
| Maleic Anhydride: | 50 |
| Isoprene: | 2.10 |
| Methanol: | 32.6 |
| Deionized Water: | 78.5 |
| Formic Acid: | 58 |
| Chlorobenzene: | 5.62 |
| Cyclohexane: | 2.02 |
| Phenol: | 9.78 |
| Bromine: | 3.09 |
| Hydrogen Bromide (at −85° C.): | 7 |
| Styrene: | ≈2.5 |

-continued

| | |
|---|---|
| Ethyl Acetate: | 6.02 |

1. Aniline + Bromine (Aqueous)

Figure 11A:
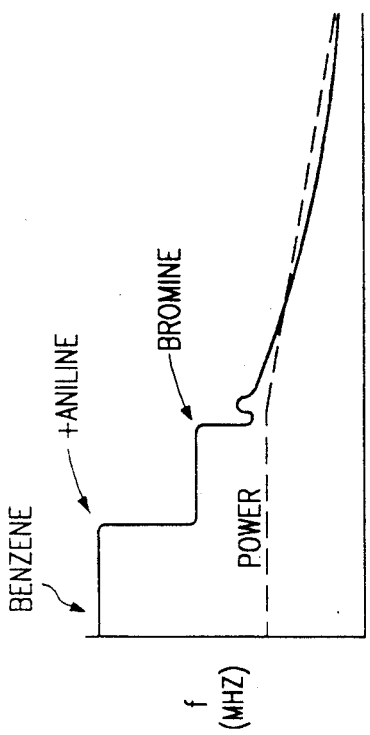
FIG. 11A shows the reaction pathways in reacting methanol with bromine.
Figure 11C:
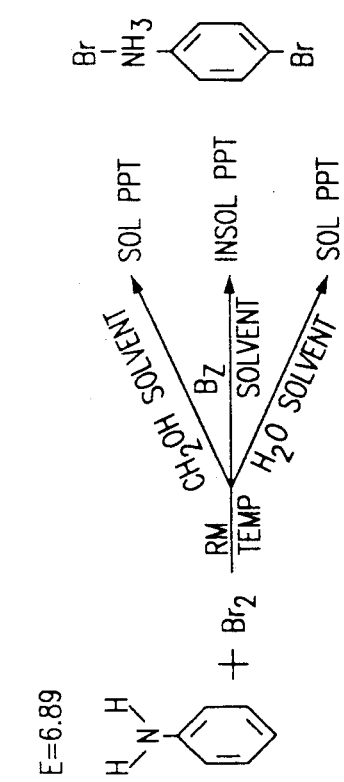
FIG. 11C schematically shows the change in oscillator frequency and insertion loss when bromine is added to a 0.05M solution of aniline in methanol.
Figure 11B:
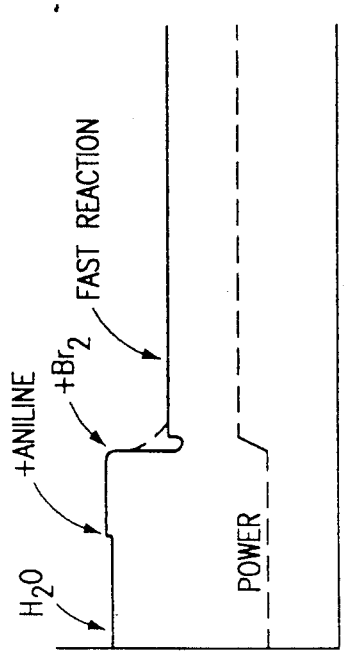
FIG. 11B schematically shows the change in oscillator frequency and insertion loss when bromine is added to a 0.05M solution of aniline in benzene.

FIG. 11A shows the reaction pathways for the reaction of liquid bromine ($Br_2$) with aniline ($C_6H_6NH_2$). This is an example of an addition reaction.

The following data shows the behavior of this reaction in water (which is a highly polar solvent), in methanol (which is slightly less polar), and in benzene (which is nonpolar).

Figure 11D:
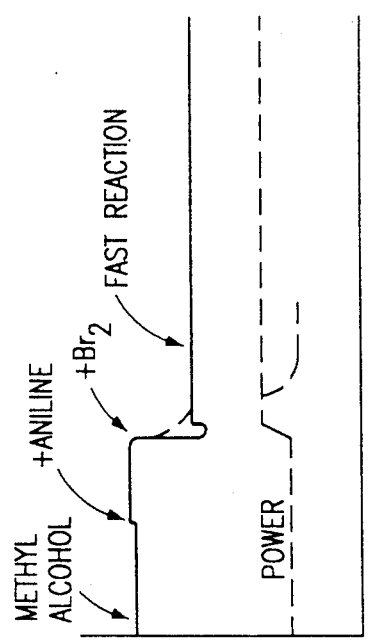
FIG. 11D schematically shows the change in oscillator frequency and insertion loss when bromine is added to a 0.05M solution of aniline in water.

In aqueous solution, as shown in FIG. 11D, the reaction went to completion very rapidly. Note that the frequency dropped very sharply as the liquid bromine was added.

At the end of the reaction, it was found that adding more water to the solution did not shift the frequency significantly. (This provides a further technique for detecting completion of the reaction.)

Note that the insertion loss decreased sharply as the bromine was added (as shown by the increase of the measured power level).

A detailed listing of the data points which are summarized in the curve of FIG. 11D is included in the Appendix below.

Some of the measured parameters for this run are here summarized in tabular form:

| | Frequency: | Insertion Loss: |
|---|---|---|
| At start: | 1146.466 MHz | −7.19 dB |
| After addition of aniline: | 1146.416 MHz | −7.17 dB |
| After addition of bromine: | 1145.908 MHz | −6.95 dB |
| After equilibration: | 1145.908 MHz | |

2. Aniline + Bromine (in Methanol)

In methanol, as shown in FIG. 11C, the reaction again proceeded rapidly to completion.

Some of the measured parameters for this run are here summarized in tabular form:

| | Frequency: | Insertion Loss: |
|---|---|---|
| At start: | 1141.133 MHz | −8.44 dB |
| After addition of aniline: | 1141.157 MHz | −8.44 dB |
| After addition of bromine: | 1140.497 MHz | −8.37 dB |
| After equilibration: | 1140.497 MHz | −8.37 dB |

3. Aniline + Bromine (in Benzene)

In benzene, this reaction is much slower, and does not produce a sedimented precipitate. In the test run, this reaction was performed with very dilute concentrations, at a temperature of 75°–78° C.

Some of the measured parameters for this run are here summarized in tabular form:

| | Frequency: | Insertion Loss: |
|---|---|---|
| At start (Benzene): | 1103.4 MHz | −4.47 dB |
| After addition of Aniline: | 1102.7 MHz | −4.49 dB |
| After addition of $Br_2$: | | −4.54 dB |
| After equilibration: (hours) | 1100.8 MHz | −4.90 dB |

4. Maleic Anhydride + Isoprene (Example 1)

This reaction is an example of the important class of Diels-Alder reactions. Such reactions are very widely used. Diels-Alder reactions are also analytically convenient, since they are highly specific to diene compounds which have two double bonds separated by exactly one saturated bond.

Maleic anhydride is a 1,3 diene (formally 1,3-diene-3-methyl butane). Isoprene is a commonly used feedstock for making synthetic rubber.

Two different sets of measurements were taken of this reaction system.

The first run, as shown in FIG. 12B, was performed at 100° F. at an initial frequency of 410 MHz. The first measurement was taken with 1.5 l of pure benzene in the system, and the frequency dropped sharply as 1 MW (1 molecular weight, i.e. a number of grams equal to the atomic weight of the substance) of maleic anhydride was added. (Maleic anhydride has a very large dielectric constant.) One MW of pure isoprene was then added. The resulting curve shows a sharp small rise in frequency as the isoprene is added, and then shows a sharp large drop as the reaction takes place. (The measured frequency also showed a more gradual subsequent drop, not shown in FIG. 12B. This is probably due to the depletion of volatile components over the course of the run.)

Some of the measured parameters for this run are here summarized in tabular form:

| | Frequency: | Insertion Loss: |
|---|---|---|
| At start (Benzene): | 406 MHz | −0.3 dB |
| After addition of Maleic Anhydride: | 390 MHz | −1.1 dB |
| After addition of Isoprene: | 391.5 MHz | −1.05 dB |
| After equilibration: | 386.9 MHz | |
| Total Shift during reaction: | $\Delta$ = 19 MHz | |

5. Maleic Anhydride + Isoprene (Example 2)

A second series of data runs studied whether any effect could be seen by reversing the order of mixing.

In this run, as shown in FIG. 12D, the starting frequency was again 410 MHz in pure benzene. The reaction temperature was set at 100° F. Isoprene was added first, in quantity sufficient to make the system concentration 1 molar (1 M). This produced a small rise in frequency. Some of the measured parameters for this run are here summarized in tabular form:

| | Frequency: | Insertion Loss: |
|---|---|---|
| At start (Benzene): | 406.5 MHz | −0.3 dB |
| After addition of Isoprene: | 406.5 MHz | −0.3 dB |
| After addition of Maleic Anhydride: | | |
| After equilibration: | 387.2 MHz | −1.5 dB |

6. Temperature Dependence of Methylated Phthalic Anhydride

Using the reaction product of isoprene + maleic anhydride (which is primarily 4-Methyl-1,2,3,6-tetrahydrophthalic anhydride), the temperature dependence of the oscillator frequency was studied. Studies of single-component systems help to show how the effects of temperature- and frequency-dependence can be factored out from measurements made using the disclosed innovative teachings. In some applications, it may also be advantageous to perform direct measurement of the conditions in a single-component system. A number of such studies have now been done.

After the isoprene/maleic anhydride reaction of FIG. 12D had gone to completion, a temperature cycle was performed to observe the temperature dependence of the oscillation frequency with the reaction products in the system. As shown in FIG. 12C, the relation of the frequency to temperature was fairly linear, at about 50 kilohertz of shift per degree fahrenheit, over a fairly wide range.

The behavior of frequency over temperature appeared to show a tail at low temperatures, i.e. the frequency became more nearly constant at the lowest temperatures, rather than following the linear relation.

7. Styrene + Maleic Anhydride

Figure 13A:
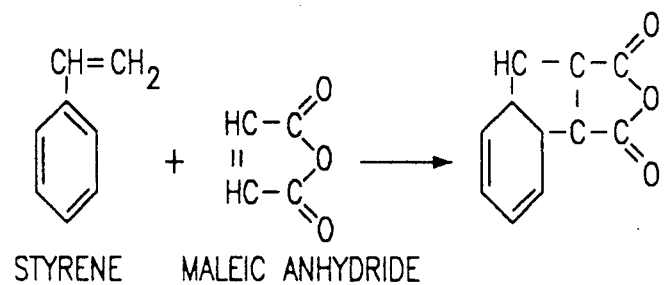
FIG. 13A shows the reaction pathways in reacting maleic anhydride with styrene.
Figure 13B:
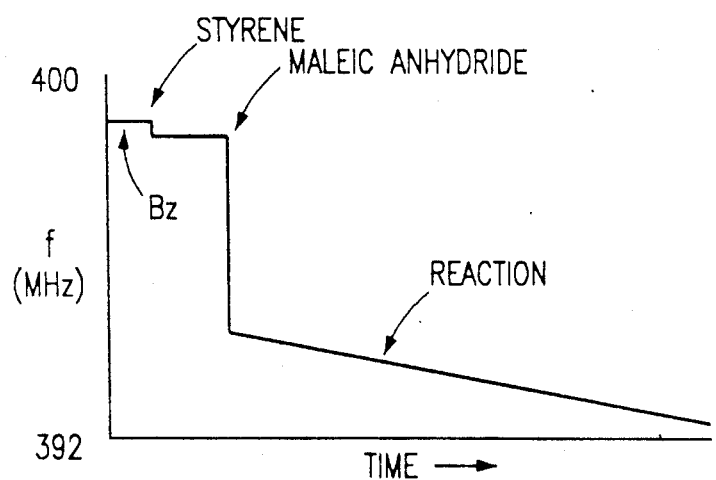
FIG. 13B schematically shows the change in oscillator frequency when maleic anhydride is added to styrene in a benzene solution.

FIG. 13A schematically shows the reaction of styrene with maleic anhydride. The experimental results of monitoring this reaction are shown in FIG. 13B.

Note that, after the sharp jump when maleic anhydride is added, the frequency continues to change fairly rapidly over time as the reaction progresses. (That is, the total frequency change over the progress of the reaction is large, and therefore the disclosed system can track the reactions's progress with high resolution.)

This reaction was conducted at 150° F., with 0.5 MW of styrene and 0.5 MW of maleic anhydride. Some of the measured parameters for this run are here summarized in tabular form:

|  | Frequency: | Insertion Loss: |
|---|---|---|
| At start (Benzene): | 398.6 MHz | −0.5 dB |
| After addition of Styrene: | 398.6 MHz | −0.5 dB |
| After addition of Maleic Anhydride: | 394.1 MHz | −0.75 dB |
| After equilibration: | 392.9 MHz | −0.75 dB |
| Total Shift during reaction: | Δ = 1.2 MHz | |

8. Methanol + Formic Acid (Esterification)

Methanol reacts with formic acid to form methyl formate and water. (This reaction is shown schematically in FIG. 14A.) This is a simple example of en esterification reaction.

Figure 14A:
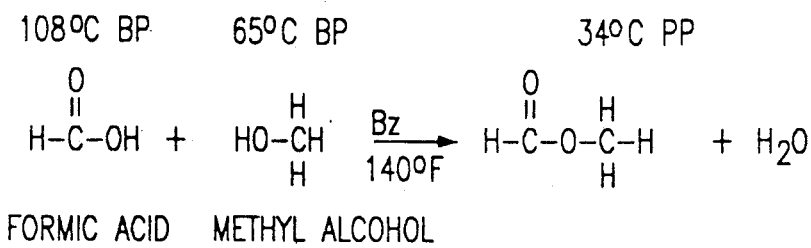
FIG. 14A shows the reaction pathways in reacting formic acid with methanol.
Figure 14B:
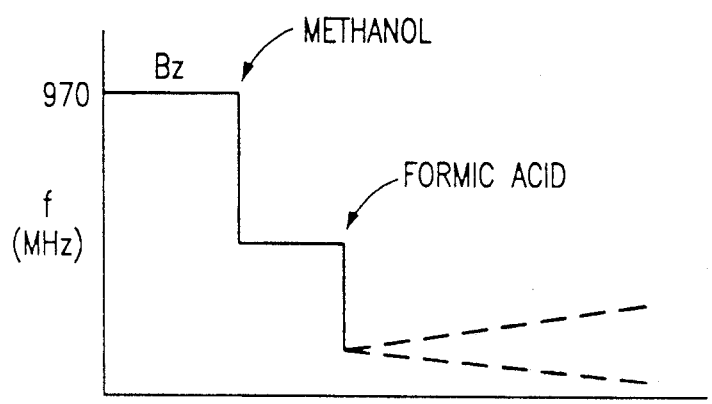
FIG. 14B schematically shows the change is oscillator frequency when formic acid is added to methanol in a benzene solution.

Results from monitoring this reaction are shown in FIG. 14B.

Figure 14C:
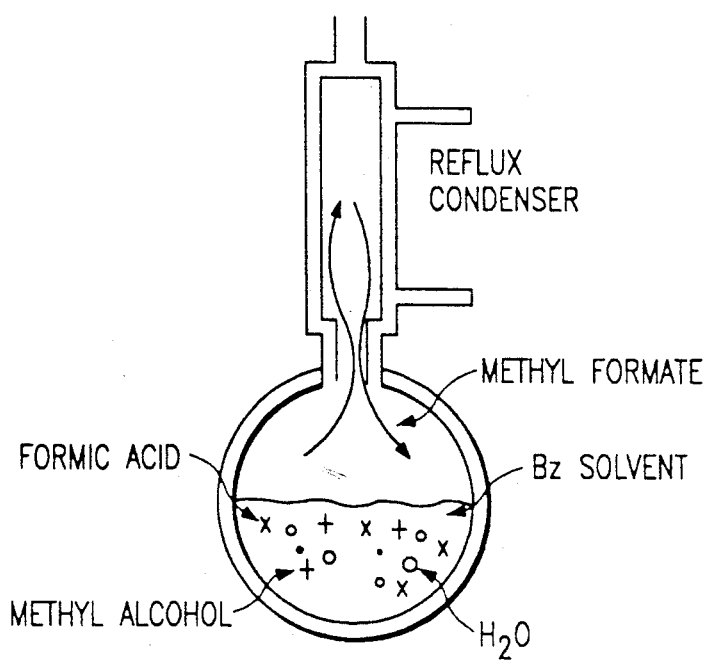
FIG. 14C schematically shows the reflux condenser arrangement used to reflux the volatile products in the reaction of FIG. 14A.

This experimental run also demonstrates several methodological alternatives. The system was initially charged with approximately a 0.5 molar concentration of methanol in benzene. After the mixture stabilized, the system was brought up to the reaction temperature (140° F. in this case). Next, formic acid was added in sufficient quantity to make up a 0.5 M solution. A very sharp frequency shift resulted. Since methyl formate is fairly volatile (boiling point 34° C.), a reflux condenser was used, as shown in FIG. 14C, to retain the product. (The methyl formate product was held in vapor/condensate system, in the condenser.)

9. Temperature Dependence of Deionized Water

Figure 15A:
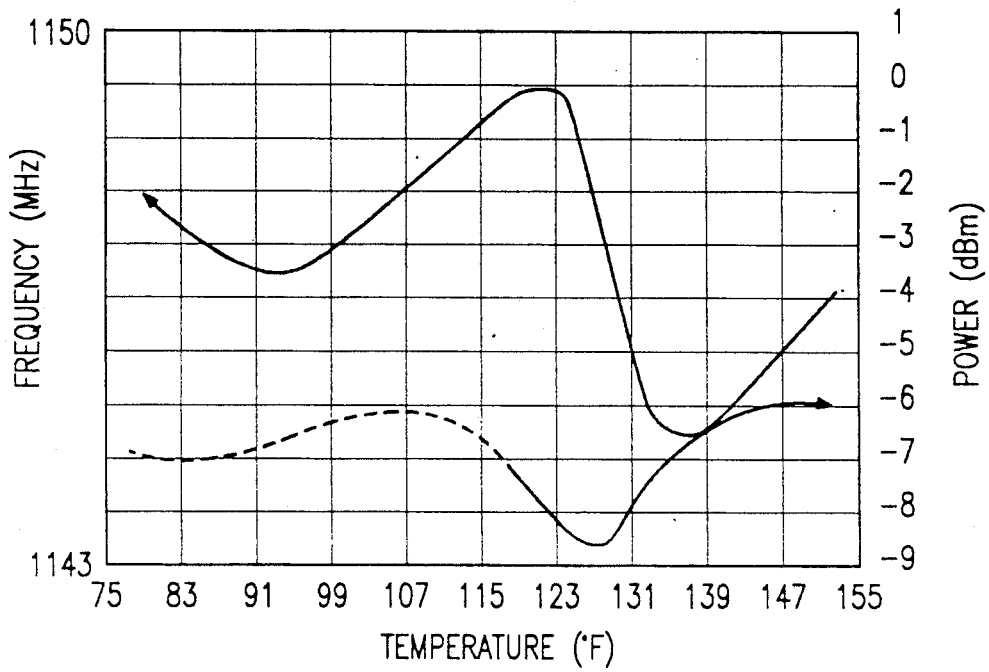
FIG. 15A shows the temperature dependence of oscillator frequency and measured power, with deionized water in the system.

The frequency dependence on temperature was also tracked for a system which includes only deionized water. In this case, very odd behavior was exhibited: the measured frequency showed sharp and repeatable dependence on temperature, including a sharply temperature-dependent peak. This curve is seen in FIG. 15A. At the peak slope of this curve, the temperature-dependence of frequency is about 500 kHz per degree Fahrenheit. Note that the insertion loss curve (the lower curve in this Figure) also shows a sharp shift at a temperature of about 127° F.

10. Temperature Dependence of Saline Solution

Figure 15B:
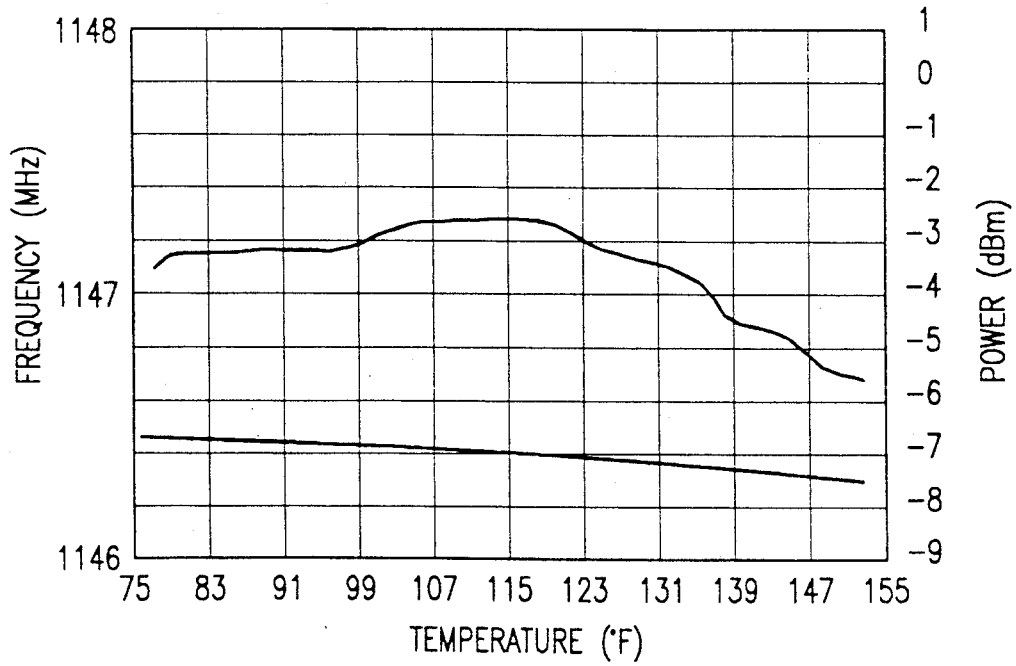
FIG. 15B repeats the measurements of FIG. 15A, using salt water instead of deionized water in the system.

For a comparison run, frequency over temperature was also observed for dilute saline (at a concentration of about 1 gram of NaCl in 1.5 liters of water). [23] In this case the frequency dependence is much flatter, as may be seen in FIG. 15B. At the peak slope of this curve, the temperature-dependence of frequency is only about 25 kHz per degree Fahrenheit.

[28]This is a quite dilute saline, with a weight percentage of about 0.07%. For comparison, the weight concentration of salts in sea water is about 3%.

11. Temperature Dependence of Cyclohexane

The temperature dependence of pure cyclohexane has also been tracked. As shown in FIG. 16C, this temperature-dependence was found to be very linear, at a frequency of about 1142 MHz, with a slope of about 44.6 kHz per degree Fahrenheit.

12. Temperature Dependence of Formic Acid/Benzene

The temperature dependence of a formic acid solution (10 ml of formic acid in 1.5 l of benzene) has also been tracked. As shown in FIG. 16A, this temperature-dependence was found to be very linear, at a frequency of about 1103 MHz, with a slope of about 50 kHz per degree Fahrenheit.

13. Temperature Dependence of Chlorobenzene

The temperature dependence of chlorobenzene has also been tracked. As shown in FIG. 16A, this temperature-dependence was found to be very linear, at a frequency of about 1103 MHz, with a slope of about 50 kHz per degree Fahrenheit.

14. Phenol + Bromine (Substitution)

Figure 17A:
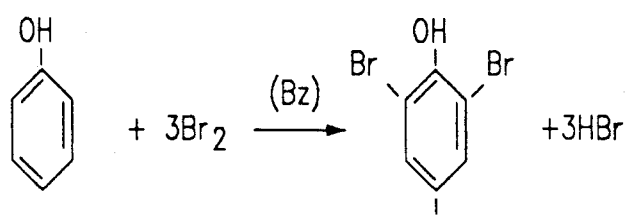
FIG. 17A shows the reaction of bromine ($Br_2$) with phenol.

FIG. 17A shows the reaction of bromine ($Br_2$) with phenol. This reaction is a convenient example of a substitution reaction.

Figure 17B:
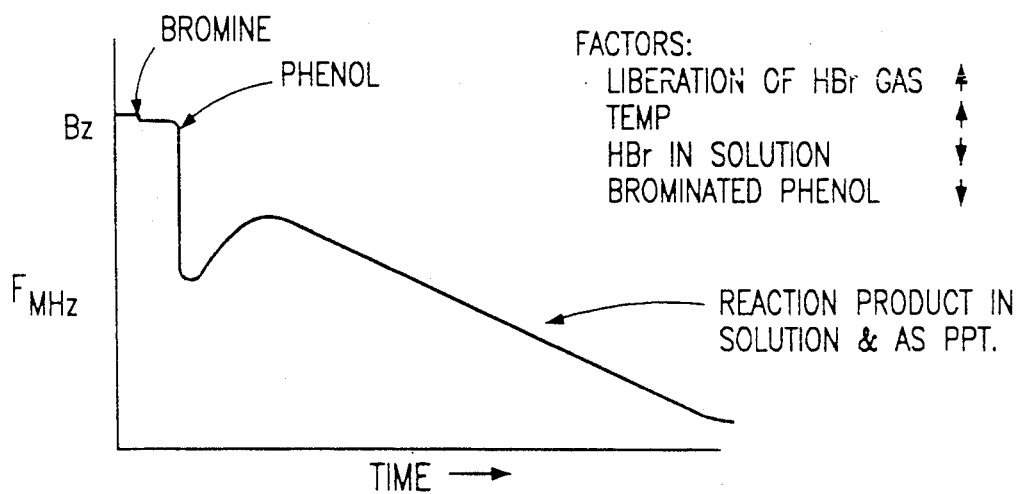
FIG. 17B shows the results of monitoring this reaction.

FIG. 17B shows the results of monitoring this reaction. Note that the frequency rises after mixing, and then gradually declines.

This reaction illustrates several important methodological challenges:

1) The reaction is exothermic, so the temperature must be carefully monitored, to avoid spurious measurement due to temperature-dependence.

2) The net physical density of the reaction mixture changes steadily as the reaction progresses.

3) One of the reaction products (at standard temperature and pressure) is a gas, which evolves while the reaction is in progress. The formation of gas bubbles in the solution, and the escape of those bubbles from the solution, will affect the electrical measurements.

Some of the measured parameters for this run are here summarized in tabular form:

|  | Frequency: | Insertion Loss: |
|---|---|---|
| At start (Benzene): | 1100.5 MHz | −4.4 dB |
| After addition of bromine: | 1100.0 MHz | −5.4 dB |
| After addition of Phenol: | | |
| After equilibration: | 1094.6 MHz | −6.5 dB |

15. Maleic Anhydride + Anthracene

Figure 18A:
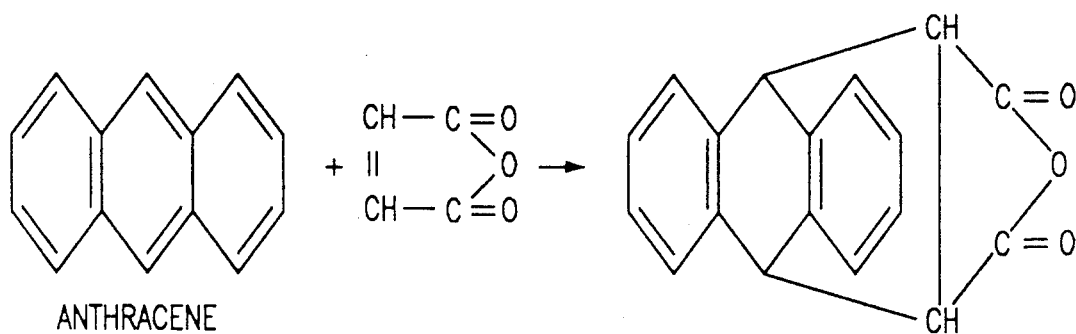
FIG. 18A shows the reaction pathways in reacting maleic anhydride with anthracene.

FIG. 18A schematically shows the reaction of Anthracene with maleic anhydride. This is a further example of a Diels-Alder reaction. It should be noted that this reaction is mildly exothermic.

Figure 18B:
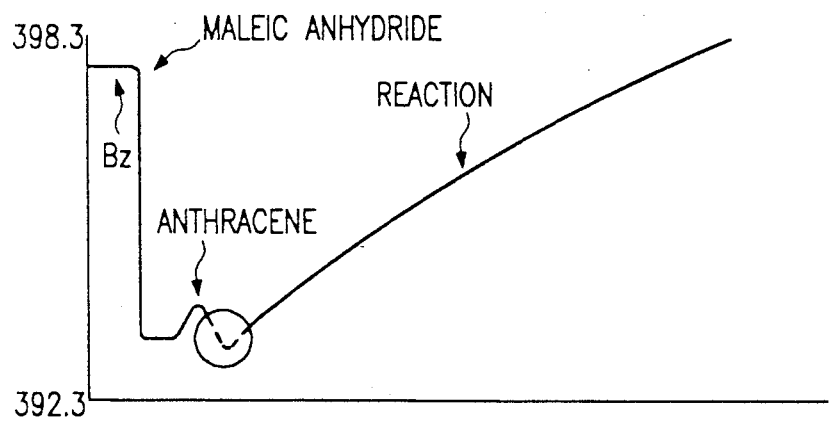
FIG. 18B schematically shows the change in oscillator frequency when maleic anhydride is added to benzene, and anthracene is added thereafter.
Figure 18C:
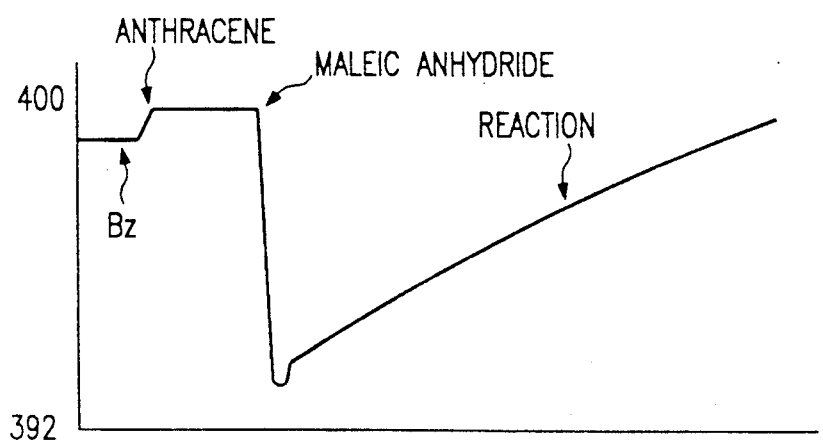
FIG. 18C schematically shows the change in oscillator frequency when anthracene is added to benzene, and maleic anhydride is added thereafter.

The two sets of experimental data summarized in FIGS. 18B and 18C show results of monitoring this reaction.

FIG. 18B shows a run where maleic anhydride was added first, and anthracene second, in a benzene solvent. (Both reagents were added in 0.5 MW quantity). The reaction temperature was 150° F. After a small rise when the anthracene is mixed in, the measured frequency shows a long increase, which represents the progress of the reaction.

Some of the measured parameters for this run are here summarized in tabular form:

|  | Frequency: | Insertion Loss: |
|---|---|---|
| At start (Benzene): | 398.2 MHz | −0.2 dB |
| After addition of maleic anhydride: | 392.8 MHz | −0.3 dB |
| After addition of anthracene: |  |  |
| After equilibration: | 397.15 MHz | −0.1 dB |

16. Anthracene+Maleic Anhydride

FIG. 18C shows a run where anthracene was added first, and maleic anhydride second, in a benzene solvent. (Both reagents were added in 0.5 MW quantity). The reaction temperature was 150° F. After a small rise when the anthracene is mixed in, and a sharp drop when the maleic anhydride is mixed in, the measured frequency shows a long increase, which represents the progress of the reaction.

Some of the measured parameters for this run are here summarized in tabular form:

|  | Frequency: |
|---|---|
| At start (Benzene): | 398.4 MHz |
| After addition of Anthracene: | 398.6 MHz |
| After addition of maleic anhydride: | 393.0 MHz |
| After equilibration (48 hours): | 397.6 MHz |

17. Saponification of Ethyl Acetate

The reaction of ethyl acetate with sodium hydroxide, in aqueous solution, yields ethanol plus sodium acetate:

$$C_2H_5COOCH_3 + Na^+ + OH^- \rightarrow_{aq} C_2H_5OH + Na^+ + CH_3COO^-.$$

In an experimental demonstration of monitoring this reaction, the starting charge was 500 ml of 0.02 M ethyl acetate, further diluted with 250 ml of water. Next, 500 ml of 0.02 M aqueous NaOH was added. This reaction was conducted at a temperature in the range of 25°–30° C., and produced a frequency and power shift as shown.

In a further state of reaction, another 250 ml of ethyl acetate solution and another 250 ml of NaOH were again added to the reaction mixture. This produced a still further frequency shift, as shown.

Figure 19:
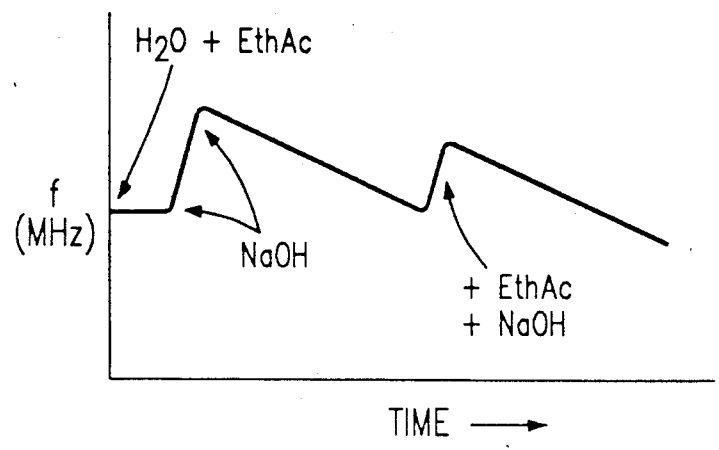
FIG. 19 schematically shows the change in oscillator frequency and power level when a sodium hydroxide solution is mixed with an ethyl acetate solution in two stages.

FIG. 19 shows how frequency and power shifted, when this reaction was monitored using the disclosed innovations.

This reaction is conventionally used in chemically instruction to show the use of conductivity measurement for reaction tracking. Since the hydroxyl ion $OH^-$ dominates the conductivity of the solution, the depletion of $OH^-$ will produce a strong swing in the conductivity.

18. Isoprene+Bromine (in Methanol)

Figure 20A:
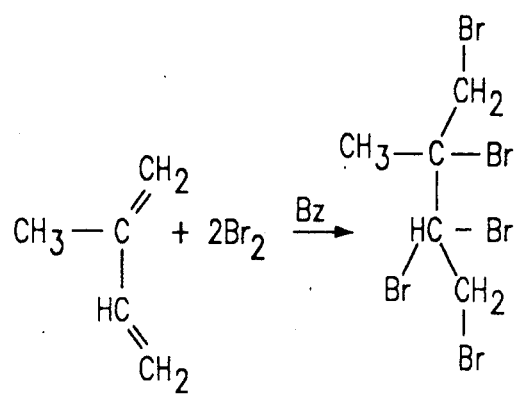
FIG. 20A shows the reaction pathways in reacting bromine with isoprene.
Figure 20B:
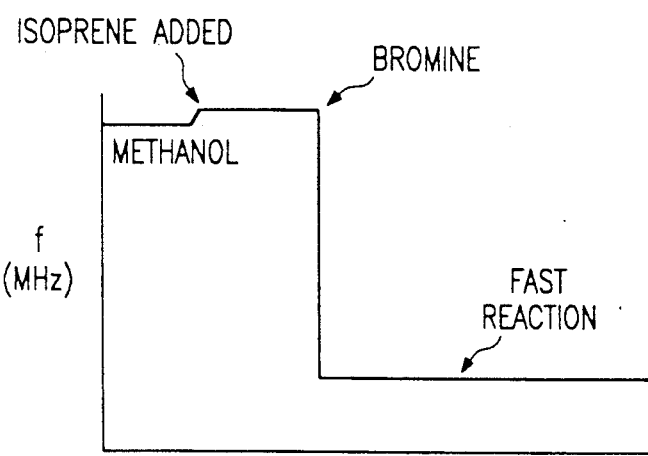
FIG. 20B schematically shows the change in oscillator frequency when bromine is added to isoprene in a methanol solution.
Figure 20C:
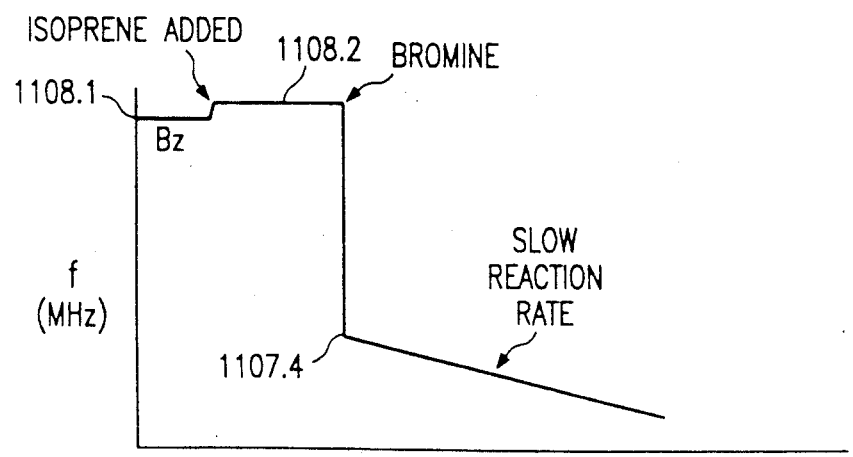
FIG. 20C schematically shows the change in oscillator frequency when bromine is added to isoprene in a benzene solution.
Figure 22:
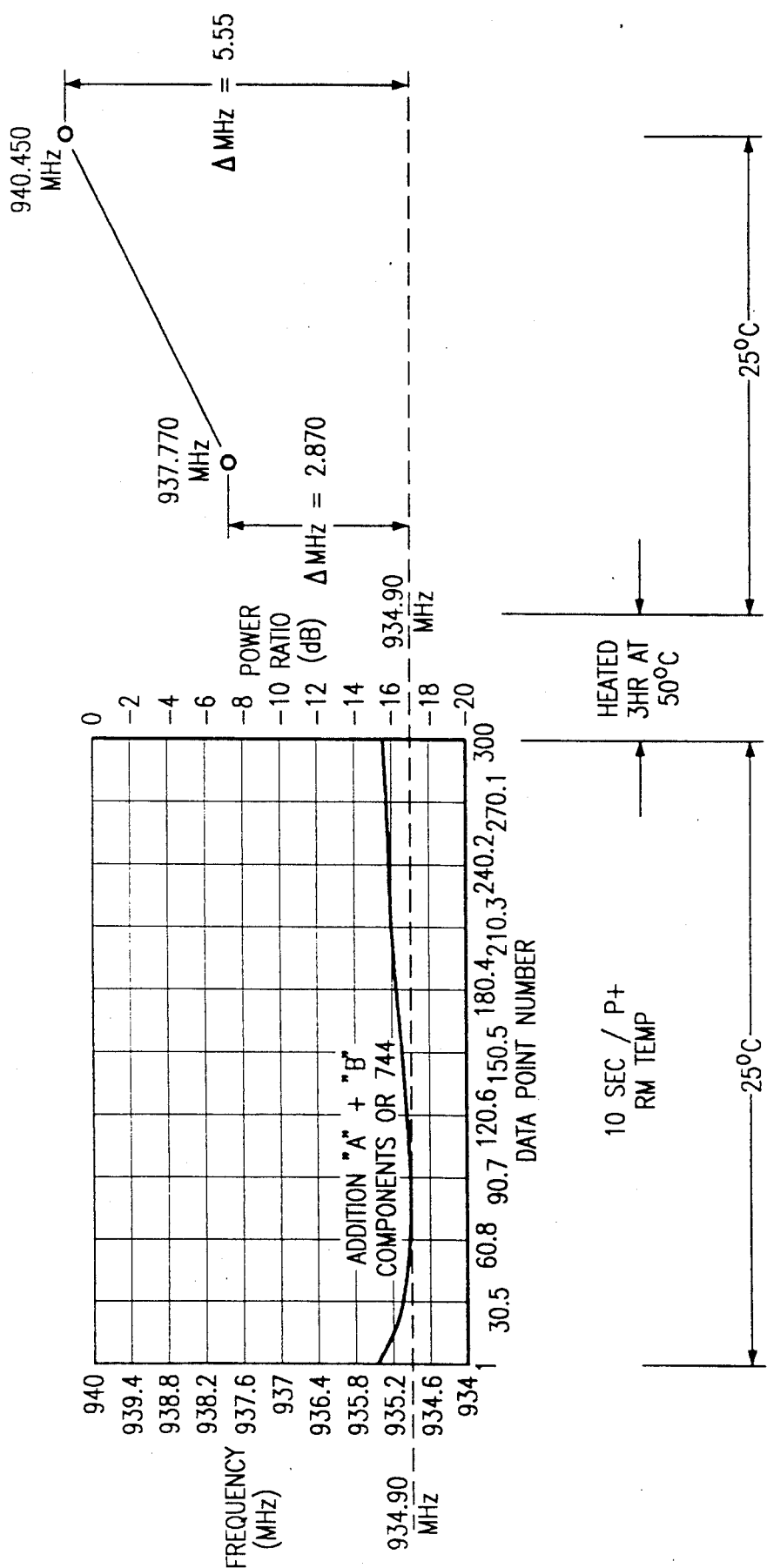
FIG. 22 schematically shows the change in oscillator frequency when the load mixture is provided by a slowly polymerizing polyurethane.
Figure 23A:
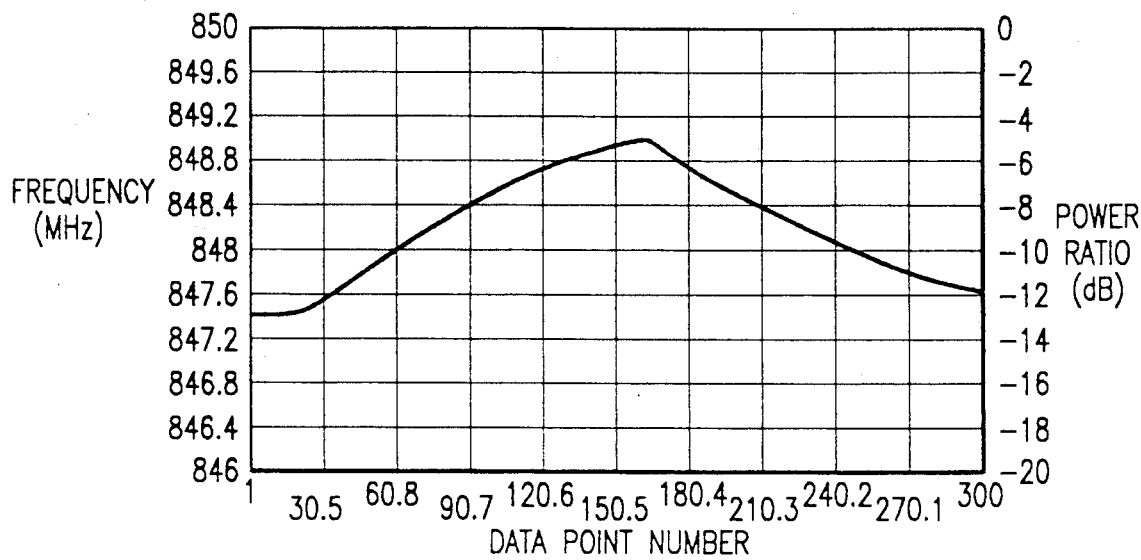
FIG. 23A and B schematically show the large oscillator frequency difference caused, in an apparatus according to the present invention, by the substitution of used engine lubricating oil, which is near the end of its service lifetime, for new lubricating oil.
Figure 23B:
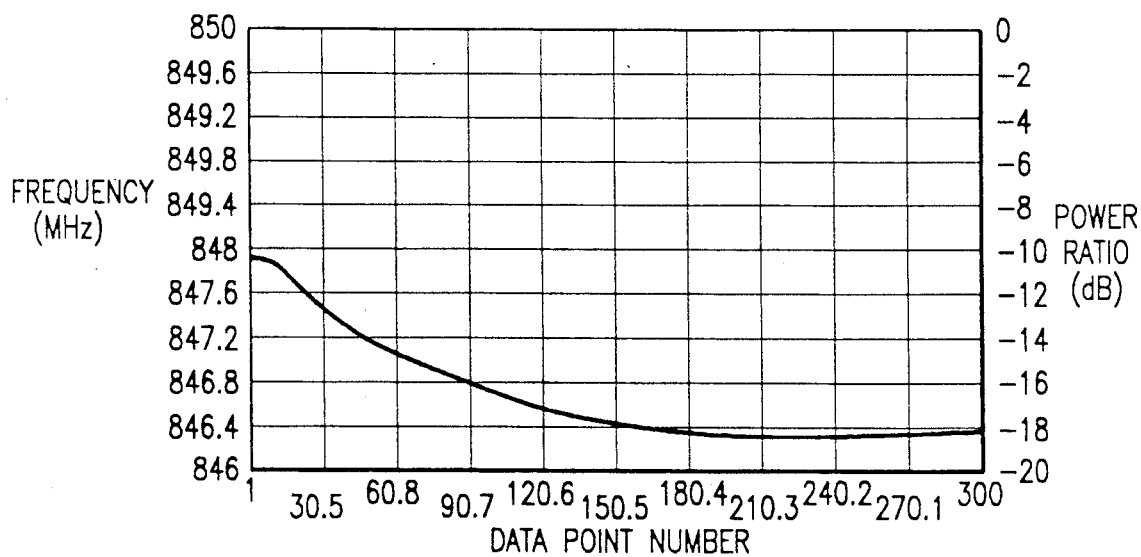

FIG. 20A schematically shows the reaction of bromine with isoprene. FIGS. 20B and 20C schematically show two sets of experimental data which show monitoring of this reaction, using the disclosed innovations.

A significant methodological point here is that isoprene boils at only 35° C., and thus may readily flash off from the reaction mixture. Thus, in these experimental runs, more isoprene was added after the reaction has apparently gone to completion, as a check for completion.

FIG. 20B shows the reaction in a polar solvent (methanol), at 74° F. Note that the reaction goes to completion rapidly.

Some of the measured parameters for this run are here summarized in tabular form:

|  | Frequency: | Insertion Loss: |
|---|---|---|
| At start (Methanol): | 1141.2 MHz | −8.1 dB |
| After addition of Isoprene: |  |  |
| After addition of bromine: |  |  |
| After equilibration: | 1140.2 MHz | −7.8 dB |
| Add excess isoprene: | 1140.2 MHz | −8.1 dB |

19. Isoprene+Bromine (in Benzene)

FIG. 20C shows the reaction in a nonpolar solvent (methanol). Note that the reaction goes to completion more slowly than the reaction of FIG. 20B. Some of the measured parameters for this run are here summarized in tabular form:

|  | Frequency: | Insertion Loss: |
|---|---|---|
| At start (Benzene): | 1108.1 MHz | −4.4 dB |
| After addition of Isoprene: | 1108.2 MHz | −4.4 dB |
| After addition of Bromine: | 1107.5 MHz | −4.4 dB |
| After reaction: | 1106.9 MHz | −4.4 dB |
| Add further 2 g Isoprene: | 1105.4 MHz |  |
| Add further 5 g Isoprene: | 1105.6 MHz |  |
| Add further 2 g Isoprene: | 1105.7 MHz |  |
| Add further 25 g Isoprene: | 1107.3 MHz |  |

20. Viscosity Dependence of α-Silica/Methanol Mixture

Figure 21:
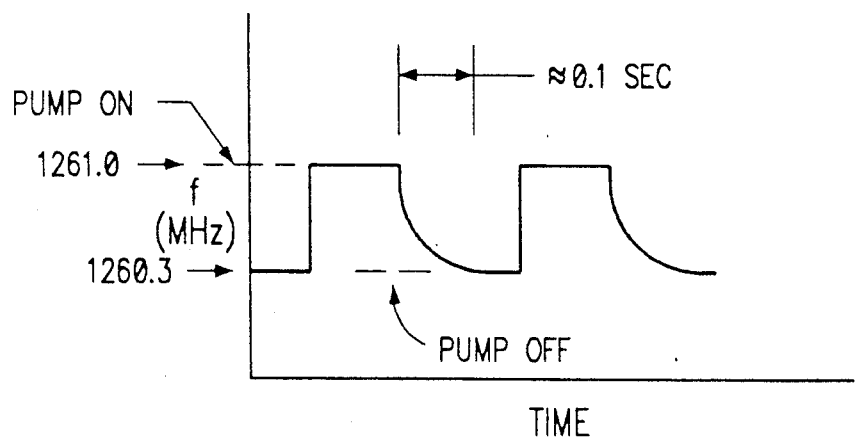
FIG. 21 schematically shows the change in oscillator frequency over time, in a solution of amorphous silica in methanol, when the circulating pump is turned on and off.

The experimental data summarized in FIG. 21 shows a different use of the disclosed innovations. This experiment measured fluid viscosity in situ. In order to dynamically modify viscosity, a thixotropic liquid was used. Thus, by switching the system pump on and off, the viscosity could be changed (by changing the forces on the thixotropic liquid).

Thus, this embodiment of the invention is not limited to thixotropic or antithixotropic compositions, but can be used to monitor viscosity in situ in a wide variety of liquid compositions.

In this experiment 50 g of finely divided amorphous silica (having a surface area of approximately 300 m²/g) was mixed into a liter of methanol. This produces a thixotropic liquid, whose viscosity is highly strain-dependent.

As shown in FIG. 21, the experimental run showed that the oscillator frequency was highly dependent on the instantaneous viscosity of the mixture. The use of a thixotropic liquid makes it particularly easy to directly measure dependence on viscosity, since viscosity can be changed, by changing physical forces applied (at the pump), with at most minimal change to other physical and chemical parameters.

The data showed a frequency shift of 700 kHz in the oscillator, depending on whether the pump was switched on or off. Note that a characteristic relaxation time of about 100 msec was seen when the pump was switched off, but the frequency rose much more sharply when the pump was switched on.

This viscosity dependence provides another example of the ability to measure short-range organization. This experiment suggests, for example, that comparable techniques might be very useful in monitoring other types of physical/chemical reactions: for example, it may be useful to detect the adhesion/cohesion changes which would indicate that the binder in a composite material has "set up".[29]

[29] Detecting setup and cure times of composite materials is a very important manufacturing need in the use of the use of composite materials (such as boron fiber plus phenolic resin) for medium- or large structural components, such as aerodynamic surfaces of aircraft.

21. Formation of Low-Density Polyurethane (Polymerization)

FIG. 20A schematically shows the reaction of a diisocyanate (primarily tolune diisocyanate in this example) with a polyol (a molecule containing multiple available —OH groups). Both of the isocyanate (—N=C=O) groups provide active sites which can react with a hydroxyl (—OH) group. The matrix of bonding from such reactions creates a macromolecule, whose mechanical properties will depend on the molecular weight and degree of cross-linking of the bonding matrix.

This reaction produces a polyurethane polymer, and is one very simple example of the many implementations of this important class of processes.

In the experimental run demonstrated, the components used were parts A and B of polyurethane mold compound PMC-744 from Smooth-On, Inc., 1000 Valley Road, Gillette N.J. 07933. This compound is specified as having a pot life of 15 minutes, a gel time of 30 minutes, a demold time of 16 hours, and a full cure time of 7 days at 25° C.

The disclosed innovations can be used with a very wide variety of other polymerization reactions. Two which are contemplated as particularly advantageous and predictable applications are in the formation of a polysulfide polymer, and in silicone polymerization reactions.

22. Monitoring Lifetime of Lubricating Oil

To demonstrate a further class of embodiments, the system was loaded in two tests, with new and with used engine oil. (The oil was Exxon brand diesel motor oil, API grade CC, viscosity 15W-40.) The used oil had been removed from a diesel truck engine after 100 hours of operation, i.e. at the end of the oil's useful life.

The measured characteristics of the two oil samples were markedly different. Both were measured over a temperature range of 50° C. to 80° C. The oscillator frequency shift, between the old and new oil, was approximately 4.7 MHz. In relation to the resolution of the disclosed system, this is a huge shift. By simple linear interpolation, this measuring technique would be estimated to have a resolution of approximately 0.02% of the oil's useful life. Even allowing a large margin of error, this is very high accuracy.

This technique can be used to monitor the aging of lubricating oil in service. Thus, oil change intervals can be reduced if needed, when unusually harsh conditions indicate that this is required. This also permits oil management to be performed far more precisely in vehicle fleets.

This technique can be particularly advantageous in aviation. Mechanical failures will very rapidly change the characteristics of the oil, and this can be detected by a monitor, constructed according to the above teachings, which is permanently installed in the aircraft.

USE OF REACTION MONITORING IN LARGER SYSTEMS

Figure 10:
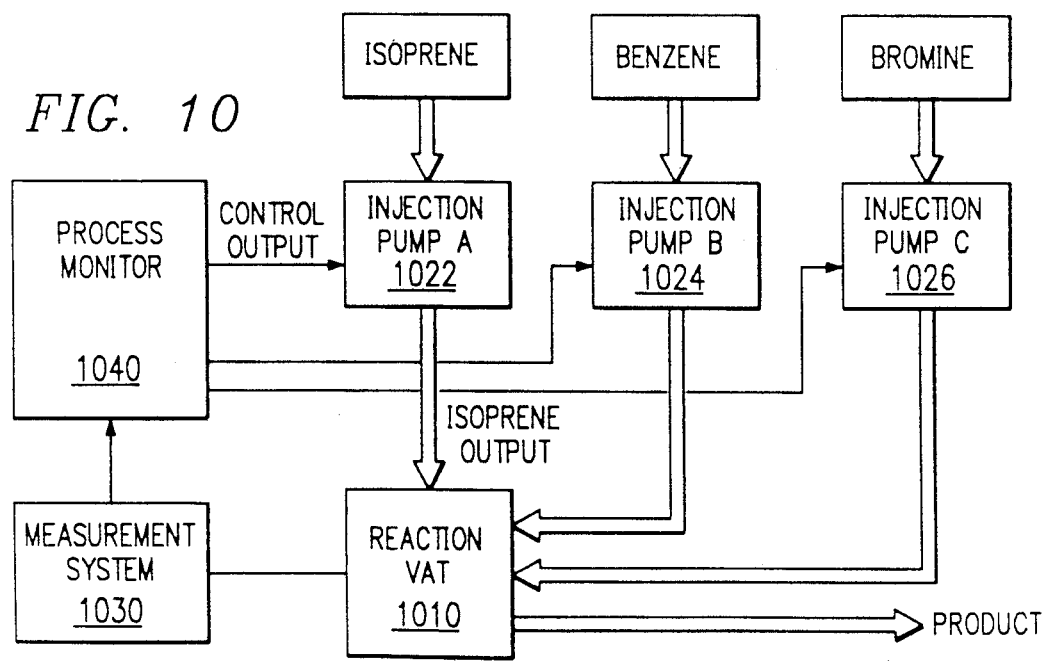
FIG. 10 shows an example of a large-scale chemical process system according to the present invention.

FIG. 10 shows an example of a large-scale chemical process system according to the present invention.

To better explain the operation of this system, it will be described with reference to a sample embodiment where a reaction vat 1010 is used to react isoprene with bromine in a benzene solvent system, in a batch or semi-continuous process.

The reaction vat 1010 is fed by three injection pumps: a first injection pump 1022, which supplies isoprene; a second injection pump 1024, which supplies benzene; and a third injection pump 1026, which supplies bromine. A product draw from the reaction vat 1010 is also shown.

A portion of the reaction vat is electrically connected to provide an electrical load for a real-time compositional measurement system 1030, which contains a free-running RF oscillator (loaded by a measurement section containing an integral portion of the contents of vat 1010) and a frequency counter, like those described above. The output of the real-time compositional measurement system is fed back to provide a measured variable input for process control system 1040 (which may be a conventional microcomputer system).

The control logic preferably implemented by the process control system 1040, in operating the system of FIG. 10, is as follows. (For clarity, this flow is described as a batch process.)

Benzene is added to the reaction vat 1010.
Isoprene is added to the reaction vat 1010.
Bromine is added to the reaction vat 1010.
Additional isoprene is metered in, by injection pump, while the frequency of the RF oscillator in measurement system is monitored, in the following control loop:
If the frequency drops as additional isoprene is added, then continue to add isoprene (because unreacted bromine is still present);
If the frequency rises as additional isoprene is added, then stop adding isoprene, and remove product (since all bromine has been consumed).

A further example of a contemplated control application is using a real-time measurement, from an electrical configuration as disclosed, to control the feed rates of feedstock flows in a three-component azeotropic distillation system.

SPECIFIC IMPLICATIONS FOR CHEMICAL INDUSTRY

The disclosed innovations will be useful in a very wide variety of applications in the chemical industry, and also in many other type of industries, including food, pharmaceuticals, and many others.

Some systems will be installed to monitor and record data that can be correlated to something of interest and be the essential counter part of those sold to the oil industry. The primary difference will be that the measurement section will have a variety of configurations since there will be few "standard" mountings. Installations will be in pipes, internal to reaction chambers, and at multiple points within distillation columns.

Most systems will not be used as simply monitors, but be a part of an interactive system controlling process parameters. Also, it is reasonable to assume that most installations will involve multiple systems since more than a single input will be necessary to control a reaction. For example, a typical installation might have separate units in feed lines, the reaction chamber, and the reaction product exit line. In some cases it may be practical to run all measurement sections from a single electronic system by multiplexing.

This equipment can be used to monitor virtually every class and type of organic reaction. This would allow control based on chemical compositional properties in both batch or continuous reactions in either liquid or gaseous systems by direct measurement.

Because the starting base components of most organic synthesis are known and tightly controlled, more specialized higher resolution equipment is possible to monitor subtle transitions. Because the dielectric range for particular chemical systems would be known, optimized equipment with $10^{-3}$ to $10^{"4}$ resolution is possible. It is also possible to add trace quantities of "tag" compounds to enhance the observation of particular intermediate reaction steps of interest in complex chemical sequences.

FURTHER MODIFICATIONS AND VARIATIONS

It will be recognized by those skilled in the art that the innovative concepts disclosed in the present application can be applied in a wide variety of contexts. Moreover, the preferred implementation can be modified in a tremendous variety of ways. Accordingly, it should be understood that the modifications and variations suggested below and above are merely illustrative. These examples may help to show some of the scope of the inventive concepts, but these examples do not nearly exhaust the full scope of variations in the disclosed novel concepts.

For another example, in some applications it may be useful to use TWO load-pulled oscillators in a single flow, and use a differential measurement between the two load stages, for more precise monitoring. This permits high-resolution measurement of trends in space or in time.

For another example, in some applications, where relatively wideband tuning of the oscillator is anticipated, it may be useful; to use two separate measurement sections which are in proximity but have different electrical lengths. Since the two measurement sections will not pass through a hop at the same frequency, such a configuration provides another way to obtain accurate frequency measurement without error due to frequency hopping. The two measurement sections can be used as loads for two separate load-pulled oscillators, or can be multiplexed onto a single oscillator.

For another example, it is possible to connect a single measurement section to two (or more) free-running oscillators running at different frequencies.

For another example, in some applications it may be useful to use to monitor the location of a phase boundary, in a continuous process.

For another example, in some applications it may be useful to monitor physical phase characteristics, such as the degree of emulsification or colloidization in a two-phase mixture.

For another example, the disclosed innovative concepts may be particularly advantageous in monitoring Biological systems, e.g. as a real-time monitor of blood chemistry.

For another example, the disclosed innovative concepts may be particularly advantageous in environmental monitoring, e.g. to provide real-time monitoring of chemical contamination. This can be used in providing systems to monitor issues such as water supply quality or acid rain.

For another example, the disclosed innovative concepts may be particularly advantageous for geological systems, e.g. for downhole monitoring or as a new electrical profiling tool for formation measurements or rock sampling.

For another example, the disclosed innovative concepts may be particularly advantageous for the food industry, for measuring the water content of a known material, or for sample analysis, or for purity monitoring (to detect tampered solutions). For similar reasons the disclosed innovative concepts may be advantageous for the pharmaceuticals industry.

For another example, the very precise compositional monitoring provided by the disclosed innovations can be used to monitor and control the fraction of a low-percentage component of a mixture. For example, this may be used to design systems in which the catalyst circulates with the reagents (and is recovered from the product), rather than using an excess of catalyst which is confined in a fixed location (using a mesh or a fluidized bed), as is conventional. A catalyst will normally be lost or consumed at a moderate rate over time, and the compositional monitoring permitted by the present invention can avoid excessive catalyst consumption, by allowing the total fraction of catalyst present to be reduced without any risk of falling below predetermined a minimum catalyst fraction. This can be particularly advantageous where the catalyst is a finely divided metal, as is common.

For another example, the very precise compositional monitoring provided by the disclosed innovations can be used in polymer synthesis to monitor and control the characteristics of the reaction mixture. As is well known to polymer chemists, there are a large number of additives which can be used to modify polymer properties by affecting the molecular weight, degree of cross-linking, and/or formation of heterogeneous domains in the product. Some of these additives are not consumed, and many of them have a large effect in very small concentrations. The sensitive measurement of compositional (and of changes in molecular bonding and conformation) permits more precise control of such additives, and also of other inputs (such as thermal curing or photochemical energy input).

For example, the disclosed methods can be used to precisely monitor changes in physical density of materials, or in the small-scale structure of materials. For example, very small changes in the solid/gas ratio of a fluidized bed can be detected, especially in the range where the gas film thickness between adjacent solid particles changes significantly. For another example, the disclosed methods may be used to monitor the degree of solid-solid linkage in a gel or aerogel.

In further alternative embodiments, the disclosed innovations can be used for dynamic monitoring (and/or for control based on dynamic monitoring) of any of the following: monitoring reaction kinetics (reaction rates); analysis of dynamic components of reaction and reactivity; analysis of isomeric components and transitional equilibrium; determination of various equilibrium constants based on the identification of particular species; determination of solubility/insolubility constants; determination of extent of completion of reaction; monitoring changes in physical phase; monitoring intermediate reaction components which may control yield or properties; monitoring/determination of reaction mechanisms; monitoring/determination of ionization/dissociation constants; monitoring the state of catalysts (e.g. solid/liquid solubility or ionic states); component characteristics from polar contributing components (e.g. with ionic groups, asymmetric unsaturated bonds, nucleophilic groups, or electrophilic groups); determination of particular component concentration.

For another example, the very precise compositional monitoring provided by the disclosed innovations can be used to rigorously monitor a product for contamination by undesired intermediates. This can be particularly advantageous in the food and pharmaceuticals industries, since it broadens the range of process which can be used economically while still meeting product purity standards.

For another example, the very precise monitoring of short-range organization, in two-phase compositions, which is provided by the disclosed innovations can be used to monitor and control the fraction of a high-cost component of a slurry, gel, or other multiphase system.

For another example, the very precise monitoring of short-range organization which is provided by the disclosed innovations can be used to monitor and control the flow characteristics of two-phase inputs to a continuous process. Chemical processes can now be designed to use slurries as inputs, and to make use of both the liquid and the solid components of the slurry, with confidence that the flow rate and composition of the slurry can be accurately controlled.

For another example, if it is desired to operate the disclosed system at higher microwave frequencies, coupling to the variable load can be accomplished with a probe into a cavity, rather than a simple coaxial line. Such probes can readily be configured to coupled primarily to the electric field, or primarily to magnetic field.

That is, a general teaching is that an electromagnetic propagation structure is both part of a fluid stream which connects its contents to a chemical system of interest, and also part of an electrical circuit from which real-time characterization of the fluid stream can be derived. This cavity should preferably not have multiple spurious resonance modes at the frequency of interest. (For example, if a coaxial line has a radius which is much smaller than a quarter-wavelength at the frequencies of interest, the frequencies where a terminated segment of that line change from inductive to capacitive will be determined merely by the effective electrical length of the line.) It is preferable, although not absolutely necessary, that the electromagnetic propagation structure should have only one class of modes in the frequency band of interest. The electromagnetic propagation structure is most preferably a shorted coaxial segment, but may less preferably be a resonant cavity or other structure.

For another example, the disclosed system can alternatively be operated at a frequency which corresponds to the second harmonic of the cavity. In such a system, the full frequency of the oscillator is preferably fed into the load, but a filter is used to extract the second harmonic component. By measuring insertion loss at the second and higher harmonics, a profile of insertion loss over a wide range can readily be obtained. (The only hardware change needed is an appropriate filter stage.)

For another example, it is not strictly necessary to use a closed chamber for the measurement section. Alternatively, An electrical probe structure could simple be placed in close proximity to the material to be monitored. (With bulk solids, this may be necessary).

For another example, the disclosed innovative systems could also be used as an analytical tool, for analysis of samples off-line.

As will be recognized by those skilled in the art, the innovative concepts described in the present application can be modified and varied over a tremendous range of applications, and accordingly their scope is not limited except by the allowed claims.

What is claimed is:

1. A system for controlling a process, comprising:
   a voltage-controlled oscillator, which includes
      a gain element capable of providing substantial gain at frequencies greater than 100 MHz;
      a feedback path, coupling the output of said gain element to the input thereof, said feedback path including a tunable resonant circuit;
   an electromagnetic propagation structure
      which is RF-coupled to load said oscillator
      and in which electromagnetic wave propagation is electrically loaded by a portion of a medium undergoing said process;
   means for monitoring the frequency and insertion loss of said oscillator to ascertain changes in the composition of the medium; and
   means for controlling one or more process variables in accordance with the output of said monitoring means.

2. The system of claim 1, wherein said electromagnetic propagation structure comprises a transmission line segment which permits only one mode of propagation at the operating frequency of said oscillator.

3. The system of claim 1, wherein said electromagnetic propagation structure comprises a shorted transmission line segment.

4. The system of claim 1, wherein said electromagnetic propagation structure includes a hollow portion therein, through which said medium undergoing said process can flow.

5. A method for controlling a reaction process, comprising the steps of:
   providing a voltage-controlled oscillator, which includes
      a gain element capable of providing substantial gain at frequencies greater than 100 MHz, and
      a feedback path, coupling the output of said gain element to the input thereof, said feedback path including a tunable resonant circuit;
   flowing a stream of said fluid medium, in which said process is expected to be taking place, through a fluid container which is electrically configured as a transmission line segment and which is electrically connected to load said oscillator;
   operating said oscillator at a frequency chosen to provide a particularly strong shift in electrical parameters in accordance with the progress of said process in said fluid medium;
   monitoring frequency and insertion loss of said oscillator to ascertain the progress of said process in said fluid medium.

6. The method of claim 5, wherein said oscillator is operated at a microwave frequency which is near a molecular resonance in said fluid medium.

7. The method of claim 5, wherein one of said controlled variables is heat flow to a particular vessel.

8. The method of claim 5, wherein one of said controlled variable is flow of an input stream to a particular vessel.

9. The method of claim 5, wherein one of said controlled variables is flow of a product stream from a particular vessel.

10. The method of claim 5, wherein one of said controlled variables is flow of a bottom product stream from a particular vessel.

11. The method of claim 5, wherein one of the products of said reaction is expected to be strongly ionic, and wherein insertion loss is measured at at least two widely separated frequencies.

12. The method of claim 5, wherein said transmission line segment has dimensions which permit only one mode of propagation at frequencies in the neighborhood of said starting frequency of said oscillator.

13. A method for monitoring changes in the small-scale structure of a medium of interest, comprising the steps of:
provising an oscillator, which includes
a gain element capable of providing substantial gain at frequencies greater than 100 MHz, and
a feedback path, coupling the output of said gain element to the input thereof, said feedback path including a tunable resonant circuit;
flowing a stream of said fluid medium, in which said process is expected to be taking place, through a fluid container which is electrically configured as a transmission line segment and which is electrically connected to load is oscillator;
operating said oscillator at a frequency chosen to provide a particularly strong shift in electrical parameters in accordance with the progress of said process in said medium;
monitoring frequency and insertion loss of said oscillator to ascertain the progress of said process in said fluid medium.

14. The method of claim 13, wherein said medium of interest is a two-phase flowable composition.

* * * * *